(12) United States Patent
Shen et al.

(10) Patent No.: US 11,555,180 B2
(45) Date of Patent: Jan. 17, 2023

(54) METHODS AND APPARATUSES FOR PATIENT-DERIVED MICRO-ORGANOSPHERES

(71) Applicants: Xilis, Inc., Durham, NC (US); Duke University, Durham, NC (US)

(72) Inventors: Xiling Shen, Chapel Hill, NC (US); David Hsu, Durham, NC (US); Jeffrey Motschman, Durham, NC (US); Daniel Delubac, Durham, NC (US); Zhaohui Wang, Durham, NC (US)

(73) Assignees: Xilis, Inc., Durham, NC (US); Duke University, Durham, NC (US)

( * ) Notice: Subject to any disclaimer, the term of this patent is extended or adjusted under 35 U.S.C. 154(b) by 0 days.

(21) Appl. No.: 16/838,010

(22) Filed: Apr. 1, 2020

(65) Prior Publication Data
US 2020/0377861 A1    Dec. 3, 2020

Related U.S. Application Data

(60) Provisional application No. 62/853,219, filed on May 28, 2019.

(51) Int. Cl.
*C12M 1/42* (2006.01)
*C12M 3/00* (2006.01)
*C12N 5/0775* (2010.01)
*C12N 5/09* (2010.01)
(Continued)

(52) U.S. Cl.
CPC ............ *C12N 5/0693* (2013.01); *C12M 21/08* (2013.01); *C12M 35/08* (2013.01); *C12N 5/0668* (2013.01); *C12N 2500/50* (2013.01)

(58) Field of Classification Search
CPC ............... C12N 5/0693; C12N 5/0668; C12N 2500/50; C12M 35/08; C12M 21/08
See application file for complete search history.

(56) References Cited

U.S. PATENT DOCUMENTS

| | | |
|---|---|---|
| 4,683,195 A | 7/1987 | Mullis et al. |
| 5,516,681 A | 5/1996 | Naughton et al. |
| 5,559,022 A | 9/1996 | Naughton |

(Continued)

FOREIGN PATENT DOCUMENTS

| | | |
|---|---|---|
| WO | WO2016/112172 A1 | 7/2016 |
| WO | WO2016/145242 A1 | 9/2016 |

(Continued)

OTHER PUBLICATIONS

Pastula et al. "Three Dimensional Gastroinestinal Organoid Cutlure in Combination with Nerves or Fibroblasts: A Method to Characterize the Gastrointestinal Stem Cell Niche" Stem Cells International (Year: 2016).*

(Continued)

*Primary Examiner* — Marcia S Noble
*Assistant Examiner* — Lauren K Van Buren
(74) *Attorney, Agent, or Firm* — Fish & Richardson P.C.

(57) ABSTRACT

Micro-Organosphers, including Patient-Derived Micro-Organospheres (PMOS s), apparatuses and methods of making them, and apparatuses and methods of using them. Also described herein are methods and systems for screening a patient using these Patient-Derived Micro-Organospheres, including personalized therapies.

20 Claims, 22 Drawing Sheets

(51) Int. Cl.
  *A61K 35/12* (2015.01)
  *G01N 33/48* (2006.01)

(56) References Cited

U.S. PATENT DOCUMENTS

| | | | |
|---|---|---|---|
| 8,512,974 B2 | 8/2013 | Murphy et al. | |
| 8,685,638 B2 | 4/2014 | Bhatia et al. | |
| 2006/0051329 A1* | 3/2006 | Lee | B01F 5/0646 424/93.7 |
| 2007/0134209 A1* | 6/2007 | Oakey | A61K 35/39 424/93.7 |
| 2011/0159522 A1 | 6/2011 | Kamm et al. | |
| 2012/0135875 A1 | 5/2012 | Ayers | |
| 2013/0137102 A1* | 5/2013 | Buchsbaum | G01N 33/6872 435/6.11 |
| 2014/0051168 A1 | 2/2014 | Vukasinovic | |
| 2014/0221225 A1* | 8/2014 | Danen | G01N 33/5005 506/9 |
| 2015/0329829 A1* | 11/2015 | Shen | G01N 33/57434 435/7.23 |
| 2016/0102365 A1 | 4/2016 | Ince | |
| 2016/0252495 A1 | 9/2016 | Ricicova et al. | |
| 2017/0145169 A1 | 5/2017 | Oakely et al. | |
| 2017/0145189 A1 | 5/2017 | Kang et al. | |
| 2017/0199173 A1* | 7/2017 | Konry | C12M 25/14 |
| 2018/0327712 A1 | 11/2018 | Williams et al. | |
| 2019/0031992 A1 | 1/2019 | Kerns et al. | |
| 2019/0105279 A1* | 4/2019 | Lipke | A61P 9/00 |

FOREIGN PATENT DOCUMENTS

| | | | | |
|---|---|---|---|---|
| WO | WO-2017216113 A2 * | 12/2017 | | C12M 23/12 |
| WO | WO2019/067795 A1 | 4/2019 | | |

OTHER PUBLICATIONS

Shen et al.; U.S. Appl. No. 17/118,586 entitled Precision drug screening for personalized cancer therapy,: filed Dec. 10, 2020.
Shen et al.; U.S. Appl. No. 17/178,210 entitled "Precision drug screening for personalized cancer therapy," filed Feb. 17, 2021.
Matsuoka et al.; Poly (ethylene glycol)-induced acceleration of free radical polymerization of methyl methacrylate: Effects of highly viscous solvent and kinetic study; Polymer journal: 42(5); pp. 368-374; May 2010.
Drost et al.; Organoids in cancer research; Nature reviews cancer; 18 (7); pp. 407-418; Jul. 2018.
Gao et al.; High-throughput screening using patient-derived tumor xenografts to predict clinical trial drug response; Nature medicine; 21 (11); pp. 1318-1325; Nov. 2015.
Mahesparan; Extracellular matrix-induced cell migration from glioblastoma biopsy specimens in vitro; Acta Neuropathologica; 97(3); pp. 231-239; Feb. 1999.
Mohamed et al.; An integrated microfiuidic flow-focusing platform for onchip fabrication and filtration of cell-laden microgels; Lab on a Chip; 19(9); pp. 1621-1632; 33 pages; (Author Manuscript); Mar. 14, 2019.
Benton et al.; In vitro microtumors provide a physiologically predictive tool for breast cancer therapeutic screening; PloS one; 10(4); e0123312; 18 pages; Apr. 2015.
Laperrousaz et al.; Direct transfection of clonal organoids in matrigel microbeads: a promising approach toward organoid-based screens; Nucleic Acids Research; 46(12); e70; 12 pages; Jul. 2018.
International Preliminary Report on Patentability in Appln. No. PCT/US2020/026275, dated Nov. 16, 2021, 10 pages.
International Search Report and Written Opinion in Appln. No. PCT/US2020/026275, dated Jun. 29, 2020, 12 pages.
International Search Report and Written Opinion in Appln. No. PCTUS21/61471, dated Mar. 1, 2022, 10 pages.
Barretina et al.; The cancer cell line encyclopedia enabies predictive modeling of anticancer drug sensitivity; 483(7391); pp. 603-607; 13 pages; (Author Manuscript); Mar. 2012.
Damiati et al.; Microfluidic devices for drug delivery systems and drug screening genes (basel); Genes; 9(2); 103; doi:10.3390/genes9020103; 24 pages; Feb. 2018.
Klein et al.; Droplet barcoding for single-cell transcriptomics applied to embryonic stem cells; Cell; 161(5); pp. 1187-1201; May 2015.
Lu et al.; Activation of the mTOR pathway by oxaliplatin in the treatment of colorectal cancer liver metastasis; PloS one; 12(1); pp. e0169439, DOI:10.1371/journal.pone.0169439, 14 pages; Jan. 2017.
Macosko et al.; Highly paraiiei genome-wide expression profiling of individuai cells using nanoliter droplets; Cell; 161(5); pp. 1202-1214; May 2015.
National Cancer Institute DCTD Division of Cancer Treatment and Diagnosis; Available plates; Approved oncology drugs set Information: a set of FDA-approved anticancer drugs to enable cancer research; 3 pages; retrieved from the internet (https://dtp.cancer.gov/organization/dscb/obtaining/available_plates.htm) on Apr. 15, 2020.
Pauli et al.; Personaiized in vitro and in vivo cancer models to guide precision medicine; Cancer Discovery; 7(5); pp. 462-477; May 2017.
Van De Wetering et al.; Prospective derivation of a living organoid bioobank of colorectal cancer patients; Cell; 161(4); pp. 933-945; May 2015.
Vlachogiannis et al.; Patient-derived organoids model treatment response of metastatic gastrointestinal cancers; Science; 359(6378); pp. 920-926; 17 pages (Author Manuscript); Feb. 2018.

* cited by examiner

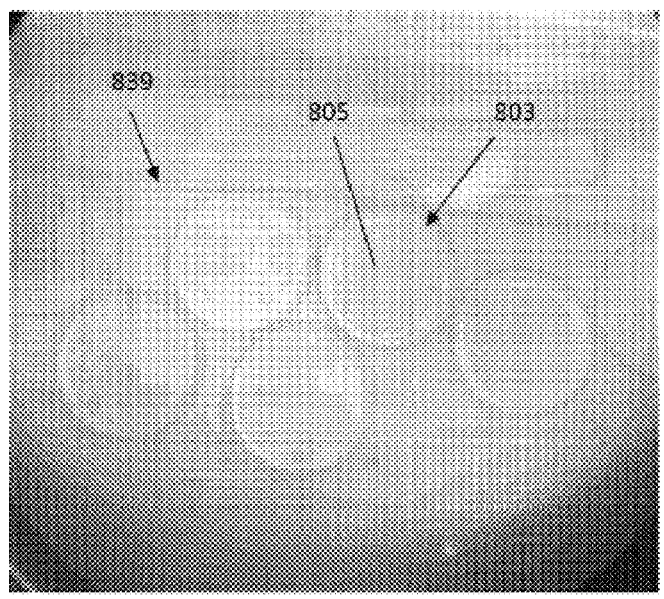
FIG. 8
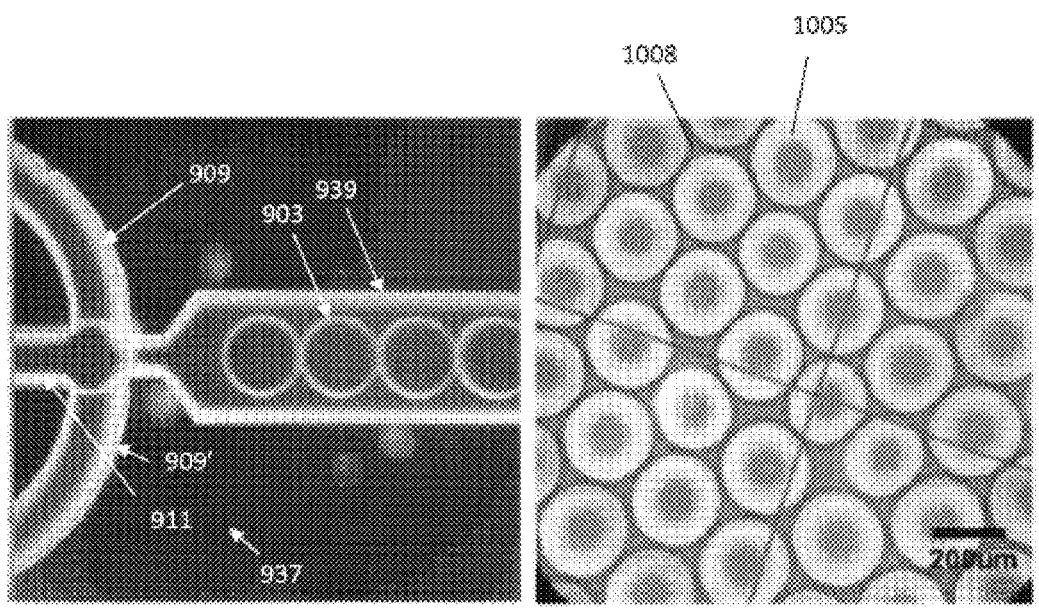
FIG. 9
FIG. 10

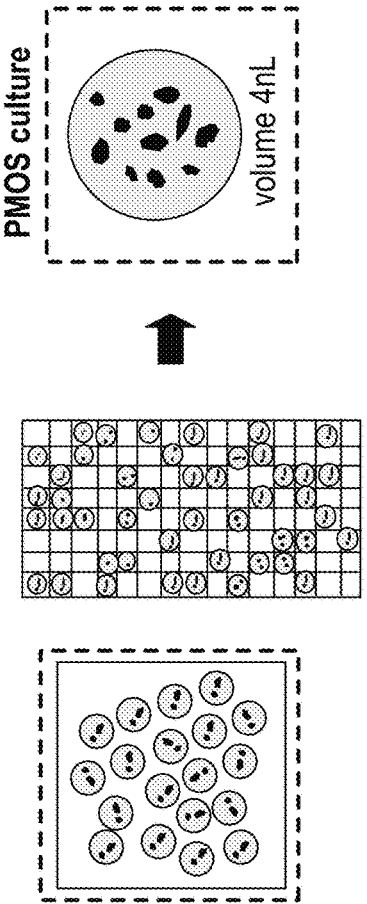
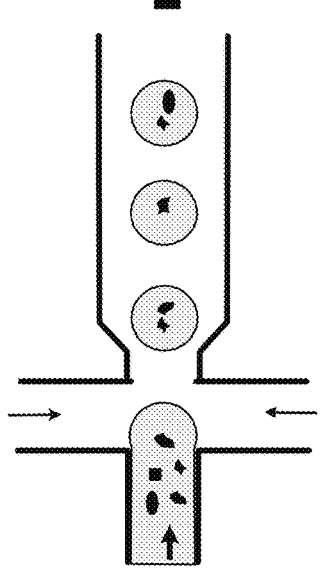
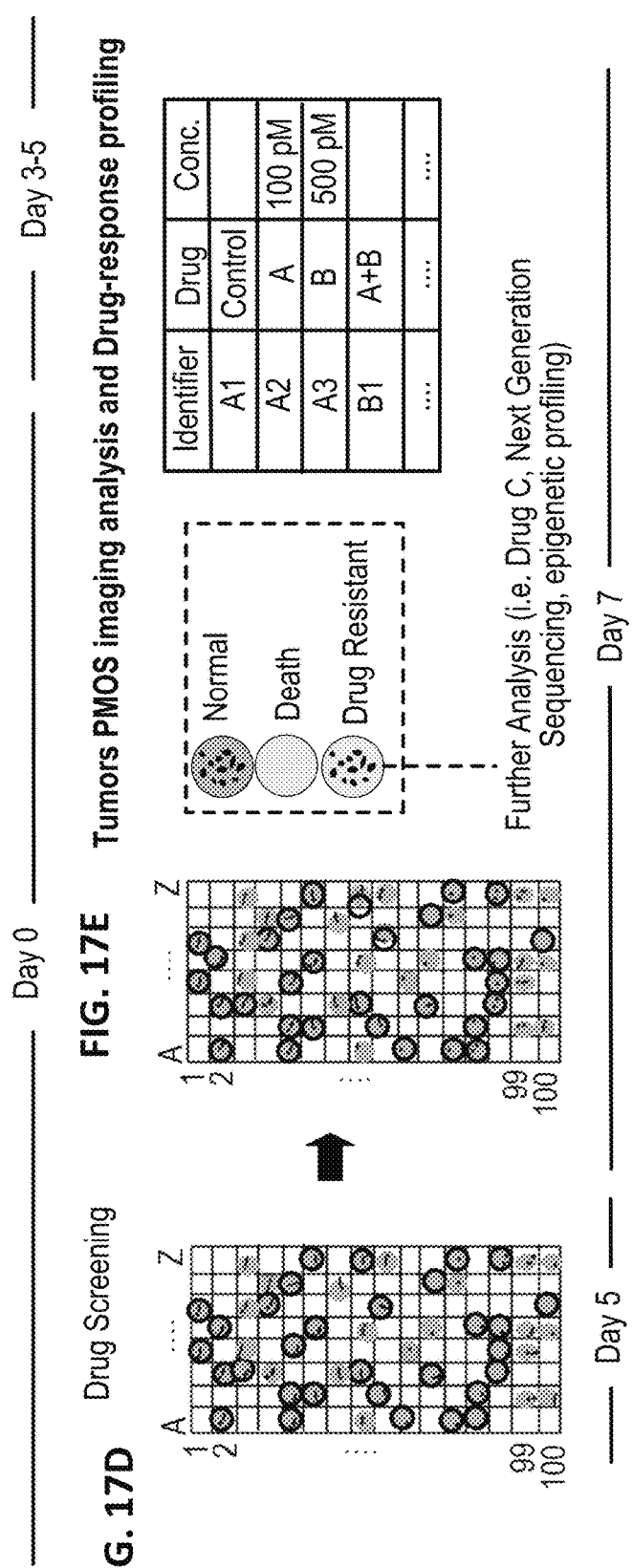
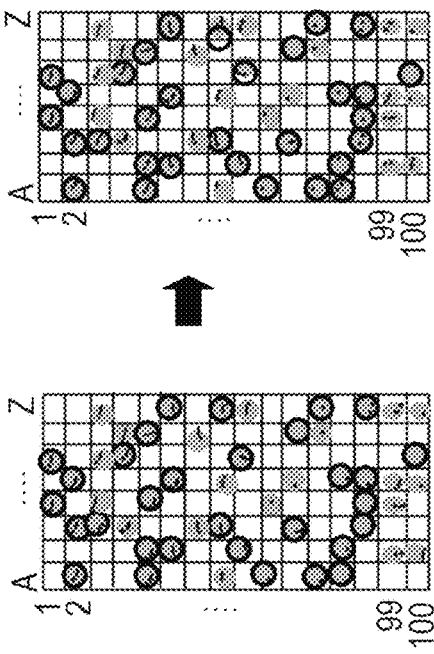
FIG. 17A Tumor Biopsy Partitioning
FIG. 17B Droplet Recovery and Microwell Plating
FIG. 17C PMOS culture, volume 4nL
FIG. 17D Drug Screening
FIG. 17E Tumors PMOS imaging analysis and Drug-response profiling
Further Analysis (i.e. Drug C, Next Generation Sequencing, epigenetic profiling)

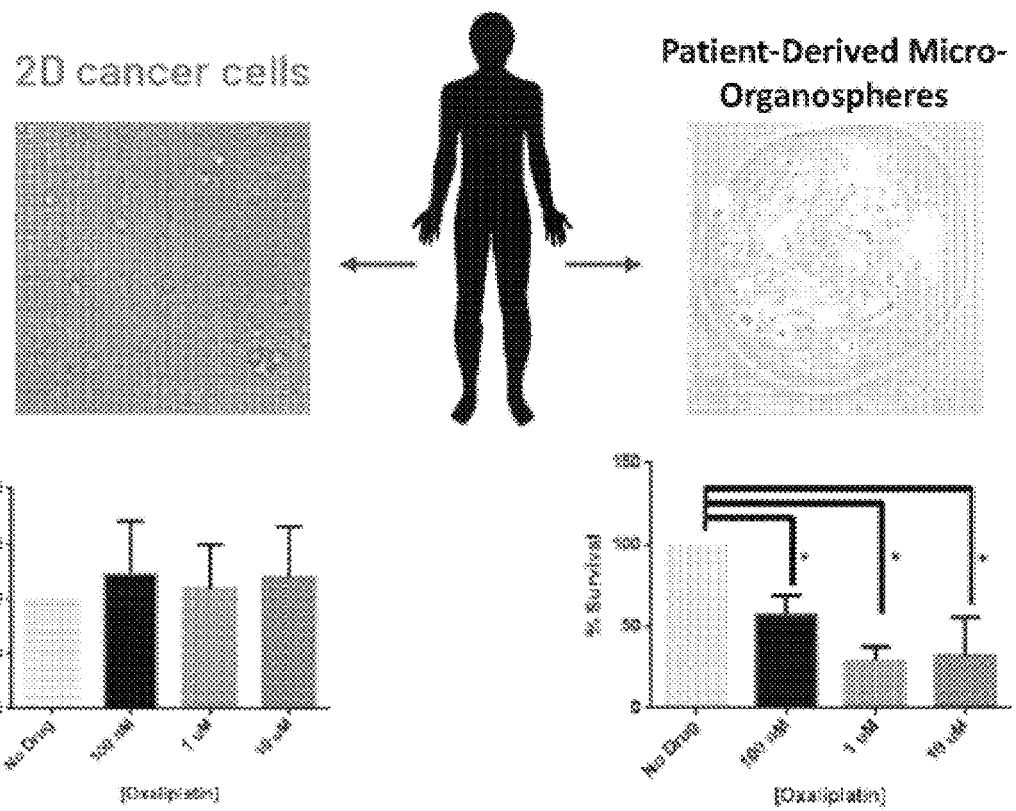
FIG. 22A Prediction: Resistant
FIG. 22B Prediction: Sensitive
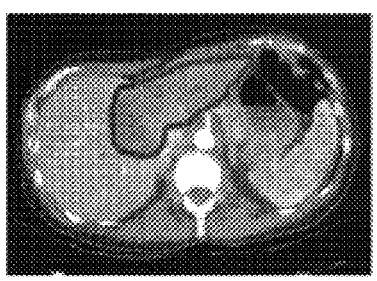
FIG. 22C Patient Tumor
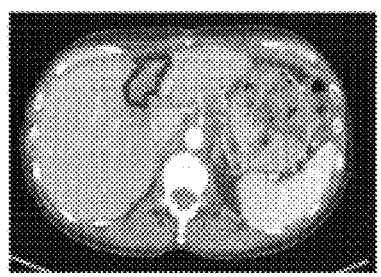
FIG. 22D Actual: RESPONSIVE

Patient-Derived Micro-Organospheres

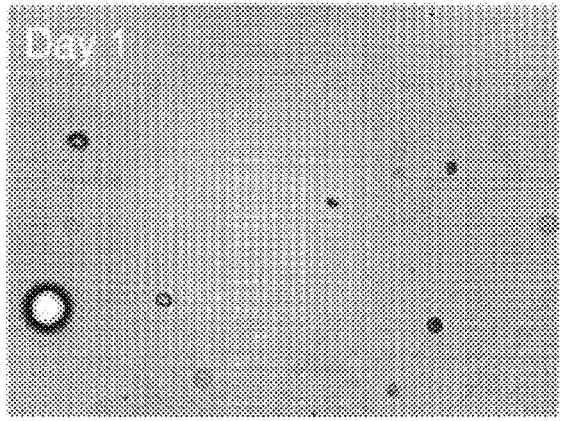 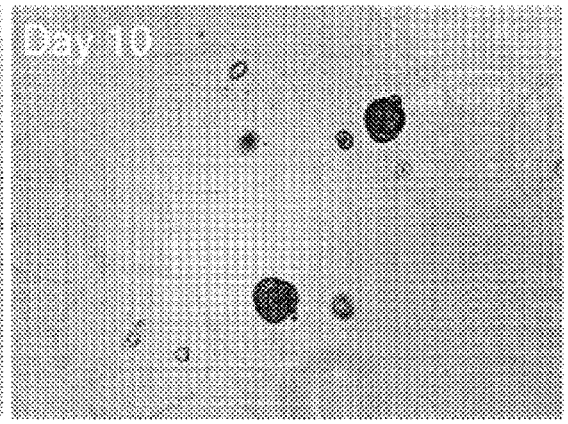
FIG. 25A　　　　　　　　　　FIG. 25B
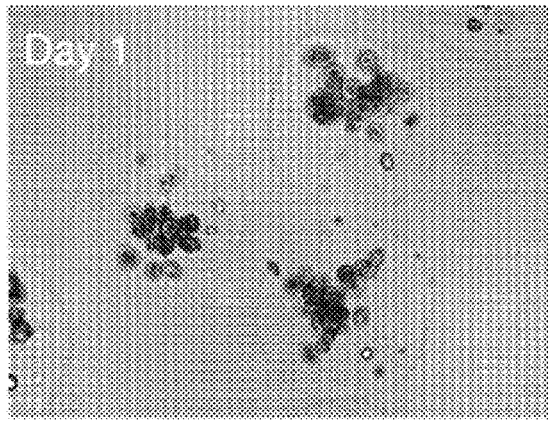 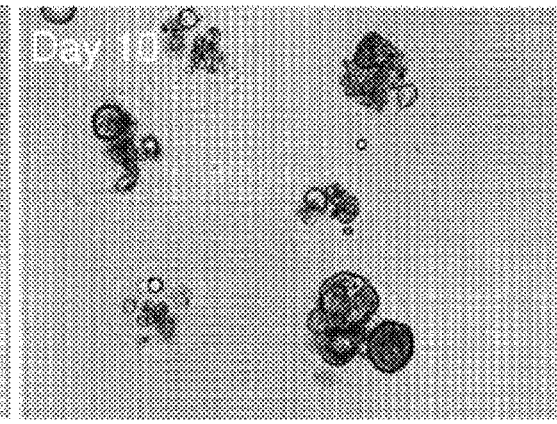
FIG. 26A　　　　　　　　　　FIG. 26B

METHODS AND APPARATUSES FOR PATIENT-DERIVED MICRO-ORGANOSPHERES

CROSS REFERENCE TO RELATED APPLICATIONS

This patent application claims priority to U.S. Provisional Patent Application No. 62/853,219, filed on May 28, 2019, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods, apparatuses and compositions of matter described herein relate to Patient-Derived Micro-Organospheres (PMOSs), and methods and apparatuses for forming PMOSs, and methods and apparatuses for using PMOSs. Specifically, described herein are methods and apparatuses for identifying one or more drug formulations that may be effective to treat a particular patient.

BACKGROUND

Model cell and tissue systems are useful for biological and medical research. The most common practice is to derive immortalized cell lines from tissue and culture them in two-dimensional (2D) conditions (e.g., in Petri dish or well plate). However, although immensely useful for basic research, 2D cell lines do not correlate well with individual patient response to therapy. In particular, three-dimensional cell culture models are proving particularly helpful in developmental biology, disease pathology, regenerative medicine, drug toxicity and efficacy testing, and personalized medicine. For example, spheroids and organoids are three-dimensional cell aggregates that have been studied. Both organoids and spheroids have limitations that reduce their efficacy, however.

Multicellular tumor spheroids were first described in the early 70s and obtained by culture of cancer cell lines under non-adherent conditions. Spheroids are typically formed from cancer cell lines as freely floating cell aggregates in ultra-low attachment plates. Spheroids have been shown to maintain more stem cell associated properties than 2D cell culture.

Organoids are in-vitro derived cell aggregates that include a population of stem cells that can differentiate into cell of major cell lineages. Organoids typically have a diameter of more than one mm diameter, and are cultured through passages. It is typically slower to grow and expand organoid culture than 2D cell culture. To generate organoids from clinical samples, it requires sufficient number of viable cells (e.g., hundreds to thousands) to start with, so it is often challenging to derive organoids from low volume samples such as biopsy, and—even if successful—it will take considerable time to expand the culture for applications such as drug testing. In addition, there is a large amount of variability in organoid size, shape and cell number. Organoids may require complex cocktails of growth factors and culture conditions in order to grow and express desired cell types.

Neither tumor spheroids nor organoids are optimal for rapid and reliable screening, particularly for personalized medicine, such as performing ex-vivo testing of drug response. For example, the practice of oncology continually faces an immense challenge of matching the right therapeutic regimen with the right patient, in addition to balancing relative benefit with risk to achieve the most favorable outcome. Patient-Derived Models of Cancer (PDMC) may include the use of organoids (including patient-derived organoids) to facilitate the identification and development of more individualized therapeutic targets. However, although retrospective studies have shown that organoid derived from resected or biopsied patient tumors correlate with patient response to therapy, there are major limitations in using organoids to guide therapy. As mentioned above, it takes months to derive and expand organoids, and particularly patient-derived organoids, from tumor samples for drug sensitivity tests, which decreases the clinical applicability, as patients cannot wait that long to receive treatment. In addition, the number of organoids needed to perform a drug screen with more than dozens of compounds currently cannot be obtained in a clinically feasible timeframe from a core biopsy specimen, which is often the only available form of tissue from patients with metastatic or inoperable cancer. The significant failure rate for deriving organoids from biopsies also prevents its use as a reliable diagnostic assay. Further, there may be a high degree of variability in the size (and potentially the response) of organoids, particularly with longer culture times, and therefore many passages.

Due to their better correlations with patient outcomes, PDMC are also being exploited to replace 2D cell lines as high-throughput screen platform for drug discovery, such as RNAi, CRISPR, and pharmacological small molecule screens. However, compared to cell lines, these PDMC models (including spheroids and organoids) are typically much slower to expand and manipulate, making it challenging and costly for high-throughput applications. The longer time required to expand these models to amplify the cell numbers also tend to allow the fastest growing clone in plastics to dominate and outcompete other clones, hence making the model more homogeneous and losing the original tissue compositions and clonal diversity. Furthermore, their relatively larger and heterogeneous sizes and limited diffusibility make them challenging for many automated fluorescence and imaging based readout assays.

Thus, what is needed are methods, compositions and apparatuses for generating patient derived tissue models (e.g., tumor models and/or non-tumor tissue models) from resection or biopsies. In particular, it would be useful to provide methods and apparatuses that may enable a large number of patient-derived tissue models having predictable and clinically relevant properties from a single biopsy, such as an 18-gauge core biopsy, which could be completed within, e.g., 7-10 days after obtaining a biopsy. This would permit robust and reliable testing and minimize delays in guiding patient-specific therapies. Furthermore, it will also be useful to generate patient derived models that can expand quickly in a highly parallel manner, generating units with smaller and more uniform sizes, better controllability for cell number per unit, and better diffusibility (e.g., via increase surface to volume ratio), for high-throughput screen applications.

SUMMARY OF THE DISCLOSURE

Described herein are Patient-Derived Micro-Organospheres (PMOSs), apparatuses and methods of making PMOSs, and apparatuses and methods of using PMOSs. Also described herein are methods and systems for screening a patient using these Patient-Derived Micro-Organospheres, including personalized therapy methods.

In general, described herein are methods and apparatuses that form and grow Patient-Derived Micro-Organospheres containing cells originating from a patient, for example, extracted from a small patient biopsy, (e.g., for quick diagnostics to guide therapy), from resected patient tissue, including resected primary tumor or part of a dysfunctional organ (e.g., for high-throughput screening), and/or from already established PDMCs, including patient-derived xenografts (PDX) and organoids (e.g., to generate Micro-Organospheres for high-throughput screening).

These PMOSs may be formed from primary cells that are normal (e.g., normal organ tissue) or from tumor tissue. For example, in some variations, these methods and apparatuses may form PMOSs from cancerous tumor biopsy tissue, enabling tailored treatments that can selected using the particular tumor tissue examined. Surprisingly, these methods and apparatuses permit the formation of hundreds, thousands or even tens of thousands (e.g., 500, 750, 1000, 2000, 5000, 10,000 or more) of PMOSs from a single tissue biopsy, within a few hours of the biopsy being removed from the patient. Dissociated primary cells from the patient biopsy may be combined with a fluid matrix material, such as a substrate basement membrane matrix (e.g., MATRIGEL), to form the micro-organosphere. The resulting plurality of Patient-Derived Micro-Organospheres may have a predefined range of sizes (such as diameters, e.g., between 10 µm and 700 µm and any sub-range therewithin), and initial number of primary cells (e.g., between 1 and 1000, and in particular lower numbers of cells, such as between 1-200). The number of cells and/or the diameter may be controlled within, e.g., +/-5%, 10%, 15%, 20%, 25%, 30%, etc. These PMOSs, when formed as described herein, have an exceptionally high survival rate (>75%, >80%, >85%, >90%, >95%) and are stable for use and testing within a very short period of time, including within the first 1-10 days after being formed (e.g., within 1 day, within 2 days, within 3 days, within 4 days, within 5 days, within 6 days, within 7 days, within 8 days, within 9 days, within 10 days, etc.). This allows for rapid tests on a potentially huge number of patient-specific and biologically relevant PMOSs which may save critical time in developing and deploying a patient therapy, such as a cancer treatment plan. The PMOSs described herein rapidly form 3D cellular structures that replicate and correspond to the tissue environment from which they were biopsied, such as a three-dimensional (3D) tumor microenvironment. The PMOSs described herein may also be referred to as "droplets". Each PMOSs may include, e.g., as part of the fluid matrix material, growth factors and structural proteins (e.g., collagen, laminin, nidogen, etc.) that may mimic the original tissue (e.g., tumor) environment. Virtually any primary cell tissue may be used, including virtually any tumor tissue.

For example, to date, all tumor types and sites tested have successfully produced PMOSs (e.g., current success rate of 100%, n=32, including cancer of the colon, esophagus, skin (melanoma), uterus, bone (sarcoma), kidney, ovary, lung, and breast from the primary site or metastatic sites including liver, omentum, and diaphragm). The tissue types used to successfully generate Micro-Organopheres may be metastasized from other locations. In some variations the PMOSs described herein can be grown from fine needle aspirate (FNA) or from circulating tumor cells (CTCs), e.g., from a liquid biopsy. Proliferation and growth is typically seen in as few as 3-4 days, and the PMOSs can be maintained and passaged for months, or they may be cryopreserved and/or used for assays immediately (e.g., within the first 7-10 days).

In particular, described herein are methods of forming Patient-Derived Micro-Organospheres. Generally, these methods include combining dissociated primary tissue cells (including, but not limited to cancer/abnormal tissue, normal tissue, etc.) with a liquid matrix material to form an unpolymerized material, and then polymerizing the unpolymerized material to form micro-Organospheres that are typically less than about 1000 µm (e.g., less than about 900 µm, less than about 800 µm, less than about 700 µm, less than about 600 µm, and in particular, less than about 500 µm) in diameter in which the dissociated primary tissue cells are distributed. The number of dissociated cells may be within a predetermined range, as mentioned above (e.g., between about 1 and about 500 cells, between about 1-200 cells, between about 1-150 cells, between about 100 cells, between about 1-75 cells, between about 1-50 cells, between about 1-30 cells, between about 1-20 cells, between about 1-10 cells, between about 5-15 cells, between about 20-30 cells, between about 30-50 cells, between about 40-60 cells, between about 50-70 cell, between about 60-80 cells, between about 70-90 cells, between about 80-100 cells, between about 90-110 cells, etc., including about 1 cell, about 10 cells, about 20 cells, about 30 cells, about 40 cells, about 50 cells, about 60 cells, about 70 cells, etc.). Any of these methods may be configured as described herein to produce Micro-Organospheres of repeatable size (e.g., having a narrow distribution of sizes).

The dissociated cells may be freshly biopsied and may be dissociated in any appropriate manner, including mechanical and/or chemical dissociation (e.g., enzymatic disaggregation by using one or more enzymes, such as collagenase, trypsin, etc.). The dissociated cells may optionally be treated, selected and/or modified. For example, the cells may be sorted or selected to identify and/or isolate cells having one or more characteristics (e.g., size, morphology, etc.). The cells may be marked (e.g., with one or more markers) that may be used to aid in selection. In some variations the cells may be sorted by a known cell-sorting technology, including but not limited to microfluidic cell sorting, fluorescent activated cell sorting, magnetic activated cell sorting, etc. Alternatively, the cells may be used without sorting.

In some variations, the dissociated cells may be modified by treatment with one or more agents. For example the cells may be genetically modified. In some variations the cells may be modified using CRISPR-Cas9 or other genetic editing techniques. In some variations the cells may be transfected by any appropriate method (e.g., electroporation, cell squeezing, nanoparticle injection, magnetofection, chemical transfection, viral transfection, etc.), including transfection with of plasmids, RNA, siRNA, etc. Alternatively, the cells may be used without modification.

One or more additional materials may be combined with the dissociated cells and fluid (e.g., liquid) matrix material to form the unpolymerized mixture. For example, the unpolymerized mixture may include additional cell or tissue types, including support cells. The additional cells or tissue may originate from different biopsy (e.g., primary cells from a different dissociated tissue) and/or cultured cells. The additional cells may be, for example immune cells, stromal cells, endothelial cells, etc. The additional materials may include medium (e.g., growth medium, freezing medium, etc.), growth factors, support network molecules (e.g., collagen, glycoproteins, extracellular matrix, etc.), or the like. In some variations the additional materials may include a drug composition. In some variations the unpolymerized mixture includes only the dissociated tissue sample (e.g., primary cells) and the fluid matrix material.

The methods may rapidly form a plurality of Patient-Derived Micro-Organospheres from a single tissue biopsy, so that greater than about 500 Patient-Derived Micro-Organospheres are formed from per biopsy (e.g., greater than about 600, greater than about 700, greater than about 800, greater than about 900, greater than about 1000, greater than about 2000, greater than about 2500, greater than about 3000, greater than about 4000, greater than about 5000, greater than about 6000, greater than about 7000, greater than about 8000, greater than about 9000, greater than about 10,000, greater than about 11,000, greater than about 12,000, etc.). The biopsy may be a standard size biopsy, such as an 18G (e.g., 14G, 16G, 18G, etc.) core biopsy. For example, the volume of tissue removed by biopsy and used to form the plurality of Patient-Derived Micro-Organospheres may be a small cylinder (taken with a biopsy needle) of between about 1/32 and 1/8 of an inch diameter and about ¾ inch to ¼ inch long, such as a cylinder of about 1/16 inch diameter by ½ inch long. The biopsy may be taken by needle biopsy, e.g., by core needle biopsy. In some variations the biopsy may be taken by fine needle aspiration. Other biopsy types that may be used include shave biopsy, punch biopsy, incisional biopsy, excisional biopsy, and the like. Typically the material from a single patient biopsy may be used to generate the plurality (e.g., greater than about 2000, greater than about 5000, greater than about 7500, greater than about 10,000, etc.) of Patient-Derived Micro-Organospheres as described above. The plurality of Patient-Derived Micro-Organospheres may be formed using an apparatus (as described herein) that may be configured to generate this large number of highly regular (size, cell number, etc.) Micro-Organospheres as described herein. In some variations these methods and apparatuses may generate the plurality or Micro-Organospheres at a rapid rate (e.g., greater than about 1 Micro-Organosphere per minute, greater than about 1 Micro-Organosphere per 10 seconds, greater than about 1 Micro-Organosphere per 5 seconds, greater than about 1 Micro-Organosphere per 2 seconds, greater than about 1 Micro-Organosphere per second, greater than about 2 Micro-Organospheres per second, greater than about 3 Micro-Organospheres per second, greater than about 4 Micro-Organospheres per second, greater than about 5 Micro-Organospheres per second, greater than about 10 Micro-Organospheres per second, greater than 50 Micro-Organospheres per second, greater than 100 Micro-Organospheres per second, greater than 125 Micro-Organospheres per second, etc.

For example, in some variations, these methods may be performed by combing the unpolymerized mixture with a material (e.g., liquid material) that is immiscible with the unpolymerized material. The method and apparatus may control the size and/or cell density of the Micro-Organospheres by, at least in part, controlling the flow of one or more of the unpolymerized mixture (and/or the dissociated tissue and fluid matrix) and the material that is immiscible with the unpolymerized mixture (e.g., a hydrophobic material, oil, etc.). For example, in some variations, these methods may be performed using a microfluidics apparatus. In some variations, multiple Micro-Organospheres may be formed in parallel (e.g., 2 in parallel, 3 in parallel, 4 in parallel, etc.). The same apparatus may therefore include multiple parallel channels, which may be coupled to the same source of unpolymerized material, or the same source of dissociated primary tissue and/or a source of fluid matrix.

The unpolymerized material may be polymerized in order to form the Patient-Derived Micro-Organospheres in a variety of different ways. In some variations the methods may include polymerizing the Micro-Organospheres by changing the temperature (e.g., raising the temperature above a threshold value, such as, for example greater than about 20 degrees C., greater than about 25 degrees C., greater than about 30 degrees C., greater than about 35 degrees C., etc.).

Once polymerized, the Patient-Derived Micro-Organospheres may be allowed to grow, e.g., by culturing and/or may be assayed either before or after culturing and/or may be cryopreserved either before or after culturing. The Patient-Derived Micro-Organospheres may be cultured for any appropriate length of time, but in particular, may be cultured for between 1 day and 10 days (e.g., between 1 day and 9 days, between 1 day and 8 days, between 1 day and 7 days, between 1 day and 6 days, between 3 days and 9 days, between 3 days and 8 days, between 3 days and 7 days, etc.). In some variations, the Patient-Derived Micro-Organospheres may be cryopreserved or assayed before six passages, which may preserve the heterogeneity of the cells within the Patient-Derived Micro-Organospheres; limiting the number of passages may prevent the faster-dividing cells from outpacing more slowly dividing cells.

In general, since the same patient biopsy may provide a high number (e.g., greater than about 2,000, greater than 3,000, greater than 4,000, greater than 5,000, greater than 6,000, greater than 7,000, greater than 8,000, greater than 9,000, greater than 10,000, etc.) cells, some of the Patient-Derived Micro-Organospheres may be cryopreserved (e.g., over half) while some are cultured and/or assayed. As will be described in greater detail herein, cryopreserved Patient-Derived Micro-Organospheres may be banked and used (e.g., assayed, passaged, etc.) later.

Thus, described herein are methods, including methods of forming a plurality of Patient-Derived Micro-Organospheres. For example, a method of forming a plurality of Patient-Derived Micro-Organospheres may include: combining a dissociated tissue sample and a fluid matrix material to form an unpolymerized mixture; forming a plurality of droplets of the unpolymerized mixture; and polymerizing the droplets to form a plurality of Patient-Derived Micro-Organospheres each having a diameter of between 50 and 500 μm with between 1 and 200 dissociated cells distributed therein.

A method, e.g., of forming a plurality of Patient-Derived Micro-Organospheres, may include combining a dissociated tissue sample and a fluid matrix material to form an unpolymerized mixture; forming a plurality of droplets from a continuous stream of the unpolymerized mixture wherein the droplets have less than a 25% variation in size; and polymerizing the droplets by warming to form a plurality of Patient-Derived Micro-Organospheres each having between 1 and 200 dissociated cells distributed within each Patient-Derived Micro-Organosphere.

In some variations, a method as described herein for forming a plurality of Patient-Derived Micro-Organospheres may include: combining a dissociated tissue sample and a fluid matrix material to form an unpolymerized mixture; forming a plurality of droplets having less than a 25% variation in size of the droplets by converging a stream of the unpolymerized mixture with one or more streams of a fluid that is immiscible with the unpolymerized mixture; polymerizing the droplets to form a plurality of Patient-Derived Micro-Organospheres having a diameter of between 50 and 500 μm with between 1 and 200 dissociated cells distributed therein; and separating the plurality of Patient-Derived Micro-Organospheres from the fluid that is immiscible.

Any of these methods may include modifying the cells within the dissociated tissue sample prior to forming the droplets.

Forming the plurality of droplets may comprise forming a plurality of droplets of the unpolymerized mixture of uniform size with less than about 25% variation in size (e.g., less than about 20% variation in size, less than about 15% variation in size, less than about 10% variation in size, less than about 8% variation in size, less than about 5% variation in size, etc.). The variations in size may also be described as a narrow distribution of size variation. For example, the distribution of sizes may include a Patient-Derived Micro-Organospheres size distribution (e.g., Micro-Organosphere diameter vs. the number of formed Micro-Organospheres) having a low standard deviation (e.g., a standard deviation of 15% or less, a standard deviation of 12% or less, a standard deviation of 10% or less, a standard deviation of 8% or less, a standard deviation of 6% or less, a standard deviation of 5% or less, etc.).

Any of these methods may also include plating or distributing the Patient-Derived Micro-Organospheres. For example, in some variations, the method may include combining Patient-Derived Micro-Organospheres from various sources into a receptacle prior to assaying. For example, the Micro-Organospheres may be placed into a multi-well plate. Thus, any of these methods may include dispensing the Patient-Derived Micro-Organospheres into a multi-well plate prior to assaying the Patient-Derived Micro-Organosphere. One or more (or in some variations in equal amounts of) Patient-Derived Micro-Organospheres may be included per well. In some variations applying the Patient-Derived Micro-Organospheres into a receptacle may include placing the Organopsheres into a plurality of chambers that are separated by an at least partially permeable membrane to permit circulation of supernatant material between the chambers. This may allow the Patient-Derived Micro-Organospheres to share the same supernatant.

In any of these methods the Patient-Derived Micro-Organospheres may be assayed. An assay may generally include exposing or treating individual Patient-Derived Micro-Organospheres to conditions (e.g., drug compositions) to determine if the drug composition has an effect on the cells of the Patient-Derived Micro-Organospheres (and in some cases, what effect it has). Assays may include exposing a subset of the Patient-Derived Micro-Organospheres (individually or in groups) to one or more concentrations of a drug composition, and allowing the Patient-Derived Micro-Organospheres to remain exposed for a predetermined time period (minutes, hours, days, etc.) and/or exposing and removing the drug composition, then culturing the Patient-Derived Micro-Organospheres for a predetermined time period. Thereafter the Patient-Derived Micro-Organospheres may be examined to identify any effects, including in particular toxicity on the cells in the Patient-Derived Micro-Organospheres, or a change in morphology and/or growth of the cells in the Patient-Derived Micro-Organospheres. In some variations assaying may include marking (e.g., by immunohistochemistry) live or fixed cells within the Patient-Derived Micro-Organospheres. Cells may be assayed (e.g., examined) manually or automatically. For example, cells may be examined to determine any toxicity (cell death) using an automated reader apparatus. In some variations assaying the plurality of Patient-Derived Micro-Organospheres may include sampling one or more of a supernatant, an environment, and a microenvironment of the Patient-Derived Micro-Organosphere for secreted factors and other effects. In any of these variations, the Patient-Derived Micro-Organospheres may be recovered following the assay for further assaying, expansion or preservation (e.g., cryopreserving, fixation, etc.) for subsequent examination.

As mentioned, virtually any assay may be used. For example, genomic, transcriptomic, proteomics, or metagenomic markers (such as methylation) may be assayed using the PMOSs described herein. Thus, any of these compositions and methods described herein may be used to identify or examine one or more markers and biological/physiological pathways, including, for example, exosomes, which may assist in identifying drugs and/or therapies for patient treatment.

Any appropriate tissue sample may be used. In some variations, the tissue sample may include comprises a biopsy sample from a metastatic tumor. For example, a tissue sample may comprise a clinical tumor sample; the clinical tumor sample may comprise both cancer cells and stroma cells. In some variations, the tissue sample comprises tumor cells and one or more of: mesenchymal cells, endothelial cells, and immune cells.

Any of the methods described herein may include initially distributing the dissociated cells from the tissue biopsy uniformly, or in some variations non-uniformly, throughout the fluid matrix material, in any appropriate concentration. For example, in some variations, the methods described herein may include combining the dissociated tissue sample and the fluid matrix material so that the dissociated tissue cell are distributed within the fluid matrix material to a density of less than $1 \times 10^7$ cells/nil (e.g., less than $9 \times 10^6$ cells/ml, $7 \times 10^6$ cells/ml, $5 \times 10^6$ cells/ml, $3 \times 10^6$ cells/ml, $1 \times 10^6$ cells/ml, $9 \times 10^5$ cells/ml, $7 \times 10^5$ cells/ml, $5 \times 10^5$ cells/ml, etc.).

In general, forming the droplet may comprise forming the droplet from a continuous stream of the unpolymerized mixture. For example, forming the droplet may comprise applying one or more convergent streams of a fluid that is immiscible with the unpolymerized mixture to the stream of unpolymerized mixture. The streams may be combined in a microfluidic device, e.g., a device having a plurality of converging channels into which the unpolymerized mixture and the immiscible fluid interact to form droplets having a precisely controlled volume. In some variations the droplets are formed (e.g., pinched off) in an excess of the immiscible material, and the droplets may be concurrently and/or subsequently polymerized to form the Patient-Derived Micro-Organosphere. For example, the region in which the streams converge may be configured to polymerize the unpolymerized mixture after the droplet has been formed, e.g., by heating, and/or the regions downstream may be configured to polymerize the unpolymerized mixture after the droplets have been formed and are surrounded by the immiscible material. In some variations the immiscible material is heated (or alternatively cooled) to a temperature that promotes polymerization of the unpolymerized material, forming the Patient-Derived Micro-Organospheres. For example, polymerizing may comprise heating the droplet to greater than 35 degrees C.

Thus, in any of these methods, forming the droplet may include forming the droplet in a fluid that is immiscible with the unpolymerized mixture. Further, any of these methods may include separating the immiscible fluid from the Patient-Derived Micro-Organospheres. For example, and of these methods may include removing the immiscible fluid from the Patient-Derived Micro-Organosphere. In general, an immiscible fluid may include a liquid (e.g., oil, polymer, etc.), including in particular a hydrophobic material or other material that is immiscible with the unpolymerized (e.g., aqueous) material.

The fluid matrix material may be a synthetic or non-synthetic unpolymerized basement membrane material. In some variations the unpolymerized basement material may comprise a polymeric hydrogel. In some variations the fluid matrix material may comprise a MATRIGEL. Thus, combining the dissociated tissue sample and the fluid matrix material may comprise combining the dissociated tissue sample with a basement membrane matrix.

The tissue sample may be combined with the fluid matrix material within six hours of removing the tissue sample from the patient or sooner (e.g., within about 5 hours, within about 4 hours, within about 3 hours, within about 2 hours, within about 1 hour, etc.).

Also described herein are methods of assaying or preserving Patient-Derived Micro-Organospheres. For example, a method may include: combining a dissociated tissue sample and a fluid matrix material to form an unpolymerized mixture; forming a plurality of droplets of the unpolymerized mixture having less than a 25% variation in a size of the droplets; polymerizing the droplets to form a plurality of Patient-Derived Micro-Organospheres having a diameter of between 50 and 700 μm with between 1 and 1000 dissociated cells distributed therein; and assaying or cryopreserving the plurality of Patient-Derived Micro-Organospheres.

In some variations a method may include: combining a dissociated tissue sample and a fluid matrix material to form an unpolymerized mixture; forming a plurality of droplets of the unpolymerized mixture; polymerizing the droplets to form a plurality of Patient-Derived Micro-Organospheres each having a diameter of between 50 and 500 μm with between 1 and 200 dissociated cells distributed therein; and cryopreserving or assaying the plurality of Patient-Derived Micro-Organospheres within 15 days, wherein the microoganoids are assayed to determine the effect of one or more agents on the cells within the Patient-Derived Micro-Organospheres.

For example, a method may include: combining a dissociated tissue sample and a fluid matrix material to form an unpolymerized mixture; forming a plurality of droplets having less than a 25% variation in a size of the droplets by converging a stream of the unpolymerized mixture with one or more streams of a fluid that is immiscible with the unpolymerized mixture; polymerizing the droplets by warming to form Patient-Derived Micro-Organospheres each having a diameter of between 50 and 500 μm with between 1 and 200 dissociated cells distributed therein; and assaying or cryopreserving the Patient-Derived Micro-Organospheres before six passages, whereby heterogeneity of the cells within the Patient-Derived Micro-Organospheres is maintained, further wherein assaying comprises assaying in order to determine the effect of one or more agents on the cells within the Patient-Derived Micro-Organosphere.

In any of these methods, the plurality of Patient-Derived Micro-Organospheres may be cryopreserved or assayed before six passages, whereby heterogeneity of the cells within the Patient-Derived Micro-Organospheres is maintained. Any of these methods may further include modifying the cells within the dissociated tissue sample prior to forming the droplets.

Forming the droplet may include forming a plurality of droplets of the unpolymerized mixture of uniform size with less than about 25% variation in size (e.g., less than about 20%, less than about 15%, less than about 10%, less than about 7%, less than about 5%, etc.).

Any of these methods may include culturing the Patient-Derived Micro-Organospheres for an appropriate length of time, as mentioned above (e.g., culturing the Patient-Derived Micro-Organospheres for between 2-14 days before assaying). For example, these methods may include removing the immiscible fluid from the Patient-Derived Micro-Organospheres before culturing. In some variations, culturing the Patient-Derived Micro-Organospheres comprises culturing the Patient-Derived Micro-Organospheres in suspension.

In general, assaying the Patient-Derived Micro-Organospheres may comprise genomically, transcriptomically, epigenomically and/or metabolically analyzing the cells in the Patient-Derived Micro-Organospheres before and/or after assaying or cryopreserving the Patient-Derived Micro-Organospheres. Any of these methods may include assaying the Patient-Derived Micro-Organosphere by exposing the Patient-Derived Micro-Organosphere to a drug (e.g., drug composition).

In any of these methods, assaying may comprise visually assaying the effect of the one or more agents on the cells in the Patient-Derived Micro-Organosphere either manually and/or automatically. Any of these methods may include marking or labeling cells in the Patient-Derived Micro-Organospheres for visualization. For example, assaying may include fluorescently assaying the effect of the one or more agents on the cells.

The Patient-Derived Micro-Organospheres described herein are themselves novel and may be characterized as a composition of matter. For example, a composition of matter may comprise a plurality of cryopreserved Patient-Derived Micro-Organospheres, wherein each Patient-Derived Micro-Organosphere has a spherical shape having a diameter of between 50 μm and 500 μm and comprises a polymerized base material, and between about 1 and 1000 dissociated primary cells distributed within the base material that have been passaged less than six times, whereby heterogeneity of the cells within the Patient-Derived Micro-Organospheres is maintained.

Also described herein are compositions of matter comprising a plurality of cryopreserved Patient-Derived Micro-Organospheres, wherein each Patient-Derived Micro-Organosphere has a spherical shape having a diameter of between 50 μm and 500 μm, wherein the Patient-Derived Micro-Organospheres have less than a 25% variation in size, and wherein each Patient-Derived Micro-Organosphere comprises a polymerized base material, and between about 1 and 500 dissociated primary cells distributed within the base material that have been passaged less than six times, whereby heterogeneity of the cells within the Patient-Derived Micro-Organospheres is maintained.

The primary cells may be primary tumor cells. For example, the dissociated primary cells may have been genetically or biochemically modified. The plurality of cryopreserved Patient-Derived Micro-Organospheres may have a uniform size with less than 25% variation in size. In some variations the plurality of cryopreserved Patient-Derived Micro-Organospheres may comprise Patient-Derived Micro-Organospheres from various sources. In any of these Micro-Organospheres, the majority of cells in each Micro-Organosphere may comprise cells that are not stem cells. In some variations, the primary cells comprise metastatic tumor cells. The primary cells may comprise both cancer cells and stroma cells. In some variations, the primary cells comprise tumor cells and one or more of: mesenchymal cells, endothelial cells, and immune cells.

The primary cells may be distributed within the polymerized base material at a density of less than, e.g., $5 \times 10^7$ cells/ml, $1 \times 10^7$ ells/ml, $9 \times 10^6$ cells/ml, $7 \times 10^6$ cells/ml, $5 \times 10^6$ cells/ml, $1 \times 10^6$ cells/ml, $9 \times 10^5$ cells/ml, $7 \times 10^5$ cells/ml, $5 \times 10^5$ cells/ml, $1 \times 10^5$ cells/ml, etc.

In general, the polymerized base material may comprise a basement membrane matrix (e.g., MATRIGEL). In some variations the polymerized base material comprises a synthetic material.

The microoganoids may have a diameter of between 50 μm and 1000 μm, or more preferably between 50 μm and 700 μm, or more preferably between 50 μm and 500 μm, or between 50 μm and 400 μm, or between 50 μm and 300 μm, or between 50 μm and 250 μm, etc. (e.g., less than about 500 μm, less than about 400 μm, less than about 300 μm, less than about 250 μm, less than about 200 μm, etc.).

As mentioned, the Patient-Derived Micro-Organospheres described herein may include any appropriate number of primary tissue cells initially in each Patient-Derived Micro-Organosphere, for example less than about 200 primary cells, or more preferably less than about 150 primary cells, or more preferably less than about 100 primary cells, or more preferably less than about 75 primary cells, or less than about 50 cells, or less than about 30 cells, or less than about 25 cells, or less than about 20 cells or less than about 10 cell, or less than about 5 cells, etc.). In some variations each Patient-Derived Micro-Organospheres includes between about 1 and 500 cells, between about 1-400 cells, between bout 1-300 cells, between about 1-200 cells, between about 1-150 cells, between about 1-100 cells between about 1-75 cells, between about 1-50 cells, between about 1-30 cells, between about 1-25 cells, between about 1-20 cells, etc.

Also described herein are apparatuses for forming Patient-Derived Micro-Organospheres, and methods of operating these apparatuses to form the Patient-Derived Micro-Organospheres. For example, described herein are methods of operating a Patient-Derived Micro-Organosphere forming apparatus comprising: receiving an unpolymerized mixture comprising a chilled mixture of a dissociated tissue sample and a first fluid matrix material in a first port; receiving a second fluid that is immiscible with the unpolymerized mixture in a second port; combining a stream of the unpolymerized mixture with one or more streams of the second fluid to form droplets of the unpolymerized mixture having a uniform size that varies by less than 25%; and polymerizing the droplets of the unpolymerized mixture to form a plurality of Patient-Derived Micro-Organospheres.

A method of operating a Patient-Derived Micro-Organosphere forming apparatus may include: receiving an unpolymerized mixture comprising a chilled mixture of a dissociated tissue sample and a first fluid matrix material in a first port; receiving a second fluid that is immiscible with the unpolymerized mixture in a second port; combining a stream of the unpolymerized mixture at a first rate with one or more streams of the second fluid at a second rate to form droplets of the unpolymerized mixture having a uniform size that varies by less than 25%, wherein the droplets are between 50 μm and 500 μm diameter; and polymerizing the droplets of the unpolymerized mixture to form a plurality of Patient-Derived Micro-Organospheres.

Any of these methods may include coupling a first reservoir containing the unpolymerized mixture in fluid communication with the first port. For example, the method may include combining the dissociated tissue sample and the first fluid matrix material to form the unpolymerized mixture. In some variations, the method includes adding the unpolymerized mixture to a first reservoir in fluid communication with the first port. These methods may include coupling a second reservoir containing the second fluid in fluid communication with the second port. Any of these methods may include adding the second fluid to a second reservoir in fluid communication with the second port. In some variations, receiving the second fluid comprises receiving an oil.

In general, these methods may include separating the second fluid (e.g., the immiscible fluid) from the plurality of Patient-Derived Micro-Organospheres. This fluid may be manually or automatically separated. For example, the second (immiscible) fluid may be removed by washing, filtering, or any other appropriate method.

Combining the streams may comprise driving the stream of the unpolymerized mixture at a first flow rate across one or more streams of the second fluid which is traveling a second flow rate. In some variations the first flow rate is greater than the second flow rate. Either or both the flow rate and/or the amount of material (e.g., the unpolymerized mixture may be present in smaller amount than the second fluid, so that the unpolymerized mixture is encapsulated in a precisely-controlled droplet, as described herein, that may then be polymerized, e.g., within the second fluid.

In some variations, combining the streams comprises driving the stream of the unpolymerized mixture across a junction into which the one or more streams of the second fluid also converge. Polymerizing the droplets may comprise heating the droplets to greater than a temperature at which the unpolymerized material polymerizes (e.g., greater than about 25 degrees C., greater than about 30 degrees C., greater than about 35 degrees C., etc.).

Any of these methods may include aliquoting the plurality of Patient-Derived Micro-Organospheres. For example, aliquoting into a multi-well dish.

Also described herein are methods of treating a patient using these Patient-Derived Micro-Organospheres and methods of assaying them. For example a method may include: receiving a patient biopsy from a tumor; determining, within 2 weeks of taking of the biopsy, that the tumor will respond to a drug formulation by: forming, from the patient biopsy, a plurality of micro-organospheres having a diameter of between 50 and 500 μm with between 1 and 200 dissociated tumor cells distributed through a polymerized base material, and exposing at least some of the Patient-Derived Micro-Organospheres to the drug formulation before the dissociated tumor cells have undergone more than five passages; and measuring an effect of the drug formulation on the cells within the at least some of the micro-organospheres to determine if the drug will treat the tumor based on the determined effect.

In some variations, these methods may include determining that the tumor is still responding to the drug formulation after one or more administrations of the drug by receiving a second patient biopsy after the patient has been treated with the drug formulation and forming a second plurality of Patient-Derived Micro-Organospheres from the second patient biopsy, exposing at least some of the second plurality of Patient-Derived Micro-Organospheres to the drug formulation, and measuring the effect of the drug formulation on cells within the at least some of the second plurality of micro-organospheres.

Determining that the tumor will respond to a drug formulation may include exposing at least some of the Patient-Derived Micro-Organospheres to a plurality of drug formulations, and reporting the measured effects for each of the drug formulations. In some variations, determining further comprises dispensing the micro-organospheres into a multi-well plate prior to assaying the Patient-Derived Micro-Organosphere.

Any of these methods may include biopsying the patient to collect the patient biopsy (or otherwise taking a tissue sample from a patient or a sample of a patient-derived tissues or cells) and/or treating the patient with the drug formulation, or assisting a physician in treating the patient (e.g., advising the physician as to which drug formulations would be effective). In general, the time between receiving the biopsy and reporting may be less than about 21 days (e.g., less than about 15 days, less than about 14 days, less than about 13 days, less than about 12 days, less than about 11 days, less than about 10 days, less than about 9 days, less than about 8 days, less than about 7 days, etc.).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4A shows the Micro-Organospheres shortly after formation (at low magnification). FIG. 4B shows a higher magnification view of some of the Micro-Organospheres of FIG. 4A taken after culturing for two days. FIG. 4C shows the Micro-Organospheres after culturing for three days. FIG. 4D shows the Micro-Organospheres after culturing for four days. FIG. 4E shows the Micro-Organospheres after culturing for five days.

FIG. 8 shows one example of an image showing a plurality of Patient-Derived Micro-Organospheres formed using an apparatus such as that shown in FIG. 7A, showing the Patient-Derived Micro-Organospheres shortly after polymerizing, suspended within a channel containing the immiscible fluid (e.g., oil) prior to being aliquoted from the apparatus.

FIG. 9 is an image of a portion of a prototype microfluidics assembly for an apparatus for forming Patient-Derived Micro-Organospheres, similar to that shown in FIG. 7C, illustrating the formation of Patient-Derived Micro-Organospheres.

FIG. 10 illustrates a plurality of Patient-Derived Micro-Organospheres as described herein, shortly after polymerization; the Patient-Derived Micro-Organospheres are suspended in the immiscible fluid.

FIG. 15A is an unstained image, while in FIG. 15B the Organospheres have been stained with Trypan blue to show that the dissociated cells in the Micro-Organospheres are alive.

FIG. 16A is an unstained image, while in FIG. 16B the Organospheres have been stained with Trypan blue (arrows) to show that the dissociated cells in the Micro-Organospheres indicated that the cell remail viable (e.g., living) within the Micro-Organosphere.

FIGS. 17A-17E illustrates one example of a method of assaying a plurality of Patient-Derived Micro-Organospheres, in this example formed from a patient tumor biopsy, to determine a drug-response profile to multiple drug formulations. The illustrated procedure takes less than two weeks (e.g., approximately one week) from biopsy to results.

FIGS. 22A-22D illustrate one example of a validation of a methods of using a plurality of Patient-Derived Micro-Organospheres as described herein to identify drug resistance. FIG. 22A illustrates the use of traditional ("2D") tumor cell assay methods, predicting drug resistance. FIG. 22B illustrates the use of one example of a Patient-Derived Micro-Organospheres method as described herein, to assay for drug resistance, predicting drug sensitivity. FIGS. 22C and 22D show that the Patient-Derived Micro-Organosphere based method accurately predicted the actual response of the tumor (drug responsive), unlike traditional cultured cells.

FIGS. 25A-25B illustrate examples of mouse liver Micro-Organospheres formed from a mouse liver tissue, having diameters of 300 µm, and 1 cell per Organosphere. FIG. 25A shows the Micro-Organospheres at day 1, and FIG. 25B shows the Micro-Organospheres at day 10.

FIGS. 26A-26B illustrate examples of mouse liver Micro-Organospheres formed from the partial hepatectomy mouse liver tissue, having diameters of 300 µm, and 25 cells per Organosphere similar to those shown in FIGS. 25A-25B. FIG. 26A shows the Micro-Organospheres at day 1, and FIG. 26B shows the Micro-Organospheres at day 10.

FIG. 27A shows the Micro-Organospheres at day 1, seeded with 40 cells/droplet. FIGS. 27B and FIG. 27C show the Micro-Organospheres at day 18. In FIG. 27B the Micro-Organospheres are hepatocyte-like structures, while FIG. 27C shows Cholangiocyte-like Micro-Organospheres.

FIG. 28A shows the Micro-Organospheres at day 1, FIG. 28B shows the Micro-Organospheres at day 3, FIG. 28C shows the Micro-Organospheres at day 5 and FIG. 28D shows the Micro-Organospheres at Day 7.

FIG. 29A shows the Micro-Organospheres at day 1, FIG. 29B shows the Micro-Organospheres at day 3, FIG. 29C shows the Micro-Organospheres at day 5 and FIG. 29D shows the Micro-Organospheres at Day 7.

FIG. 33A shows that the sizes of the tissue in the mouse liver Micro-Organospheres in the control group are relatively large (as indicated by the arrows). In contrast, in FIG. 33A, showing the acetaminophen (10 mM) treatment group, the tissue in most of the Micro-Organospheres is smaller and contains many dead cells.

FIG. 34A shows typical human liver Micro-Organospheres observed in the control group including tissue structures (indicated by the arrows). FIG. 34B shows Micro-Organospheres in an acetaminophen (10 mM) treatment group, showing atypical tissue structures (arrows) and debris.

DETAILED DESCRIPTION

Figure 1A:
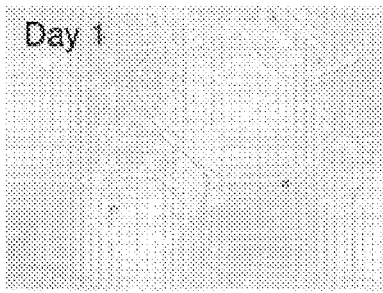
FIGS. 1A to 1C illustrate Patient-Derived Micro-Organospheres formed as described herein to include a single dissociated primary tissue cell per Micro-Organosphere, cultured for one day after forming (FIG. 1A), cultured for three days after forming (FIG. 1B), and cultured for seven days after forming (FIG. 1C). The cells originate from colorectal cancer (CRC) tissue.

In general, described herein are Patient-Derived Micro-Organospheres, methods and apparatuses for forming them, and methods and apparatuses for using them, e.g., to assay for tissue (including, but not limited to cancerous tissue) responses.

The Patient-Derived Micro-Organospheres described herein are typically spheres formed from dissociated primary cells distributed within the base material. These Patient-Derived Micro-Organospheres ("PMOSs" or "Organospheres") may have a diameter of between about 50 µm and about 500 µm (e.g., between about 50 µm and about 400 µm, about 50 µm and about 300 µm, about 50 µm and about 250 µm, etc.), and may initially contain between about 1 and 1000 dissociated primary cells distributed within the base material (e.g., between about 1 and 750, between about 1 and 500, between about 1 and 400, between about 1 and 300, between about 1 and 200, between about 1 and 150, between about 1 and 100, between about 1 and 75, between about 1 and 50, between about 1 and 40, between about 1 and 30, between about 1 and 20, etc.).

Surprisingly, despite their small size (often between about 50-250 µm), and low cell density (e.g., often less than 100 cells per Micro-Organosphere), these Micro-Organosphere may be used immediately or cultured for a very brief period of time (e.g., 14 days or less, 10 days or less, 7 days or less, 5 days or less, etc.) and may allow the cells within the Micro-Organosphere to survive while maintaining much, if not all, of the characteristics of the tissue, including tumor tissue, from which they were extracted. The survival rate of the cells within the Micro-Organospheres is remarkably high, and the Micro-Organospheres may be cultured for days (or weeks) through multiple passages, in which the cells will divide, cluster and form structures similar to the parent tissue. Also surprisingly, in some variations, the cells from the dissociated tissue within the Micro-Organosphere forms morphological structures inside even the smallest Micro-Organospheres; although in some applications, the presence of such structures is not necessary for the utility of these Micro-Organospheres (e.g., they may be used before substantial structural reorganization has occurred) in some variations they may be particularly useful.

The methods and apparatuses described herein for forming and using Micro-Organospheres may be used to create many (e.g., greater than 10,000) Patient-Derived Micro-Organospheres from a single biopsy. These Micro-Organospheres may be used screen for drug compositions that may predict what therapies may be effectively applied to the patient from whom the biopsy was taken. This may be useful, for example, in toxicity screen for drugs or other chemical compositions, from healthy normal tissue and/or from cancerous (e.g., tumor) tissue. In particular, the Patient-Derived Micro-Organospheres, methods and apparatuses for forming them and methods and apparatuses for testing them may be used for screening to identify one or more drug compositions that may effectively treat the patient (e.g., a cancer patient) prior to undergoing the drug therapy. This may allow, for example, very rapid screening of a cancer patient before they would otherwise undergo months of chemotherapy that may not be effective for them.

Thus, described herein are high-throughput drug screening methods (and apparatuses for performing these methods) using a single patient-specific biopsy (or other appropriate tissue/cell source). Described herein are droplet formed Patient-Derived Micro-Organospheres that may be formed from patient-derived tumor samples that have been dissociated and suspended in a basement matrix (e.g., MATRIGEL). The Micro-Organospheres can be patterned onto a microfluidic microwell array, to be incubated, and dosed with drug compounds. This miniaturized assay maximizes the use of tumor samples, and enables more drug compounds to be screened from a core biopsy at much lower cost per sample.

Patient-derived models of cancer (PDMC), such as cell lines, organoids and patient-derived xenografts (PDXs) are increasingly being accepted as "standard" preclinical models to facilitate the identification and development of new therapeutics. For example, large-scale drug screens of cell lines and organoids derived from cancer patients have been used to identify sensitivity to a large number of potential therapeutics. PDXs are also used to predict drug response and identify novel drug combinations. Although precision medicine strategies are in development through the exploration of these various PDMC models, there are substantial barriers to their effective use. For example, patient derived organoids (PDO) are believed to be the most accurate in depicting patient tumors, as studies have shown that phenotypic and genotypic profiling of organoids often show a high degree of similarity to the original patient tumors. Unfortunately, at least two limitations hinder the use of PDO to guide therapy. Firstly, it takes several months to develop and test drug sensitivity in organoids, which decreases the clinical applicability. Secondly the number of organoids obtained from a clinically relevant 18-gauge core biopsy is not sufficient to perform high throughput drug screen. Ideally, an assay should be performed from a single core biopsy within 7-10 days. The Micro-Organospheres and methods of making and using them described herein may address these clinical limitations.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

The term "an unpolymerized mixture" is used herein to refer to a composition comprising biologically-relevant materials, including a dissociated tissue sample and a first fluid matrix material. The fluid matrix material is typically a material that may be polymerized to form a support or support network for the dissociated tissue (cells) dispersed within it. Once polymerized, the polymerized material may form a hydrogel and may be formed or and/or may include proteins forming the biocompatible medium, in addition to the cells. A suitable biocompatible medium for use in accordance with the presently-disclosed subject matter can typically be formed from any biocompatible material that is a gel, a semi-solid, or a liquid, such as a low-viscosity liquid, at room temperature (e.g., 25° C.) and can be used as a three-dimensional substrate for cells, tissues, proteins, and other biological materials of interest. Exemplary materials that can be used to form a biocompatible medium in accordance with the presently-disclosed subject matter include, but are not limited to, polymers and hydrogels comprising collagen, fibrin, chitosan, MATRIGELTM (BD Biosciences, San Jose, Calif.), polyethylene glycol, dextrans including chemically crosslinkable or photo-crosslinkable dextrans, and the like, as well as electrospun biological, synthetic, or biological-synthetic blends. In some embodiments, the biocompatible medium is comprised of a hydrogel.

The term "hydrogel" is used herein to refer to two- or multi-component gels comprising a three-dimensional network of polymer chains, where water acts as the dispersion medium and fills the space between the polymer chains. Hydrogels used in accordance with the presently-disclosed subject matter are generally chosen for a particular application based on the intended use of the structure, taking into account the parameters that are to be used to form the Micro-Organospheres, as well as the effect the selected hydrogel will have on the behavior and activity of the biological materials (e.g., cells) incorporated into the biological suspensions that are to be placed in the structure. Exemplary hydrogels of the presently-disclosed subject matter can be comprised of polymeric materials including, but not limited to: alginate, collagen (including collagen types I and VI), elastin, keratin, fibronectin, proteoglycans, glycoproteins, polylactide, polyethylene glycol, polycaprolactone, polycolide, polydioxanone, polyacrylates, polyurethanes, polysulfones, peptide sequences, proteins and derivatives, oligopeptides, gelatin, elastin, fibrin, laminin, polymethacrylates, polyacetates, polyesters, polyamides, polycarbonates, polyanhydrides, polyamino acids carbohydrates, polysaccharides and modified polysaccharides, and derivatives and copolymers thereof as well as inorganic materials such as glass such as bioactive glass, ceramic, silica, alumina, calcite, hydroxyapatite, calcium phosphate, bone, and combinations of all of the foregoing.

With further regard to the hydrogels used to produce the Micro-Organospheres described herein, in some embodiments, the hydrogel is comprised of a material selected from the group consisting of agarose, alginate, collagen type I, a polyoxyethylene-polyoxypropylene block copolymer (e.g., Pluronic® F127 (BASF Corporation, Mount Olive, N.J.)), silicone, polysaccharide, polyethylene glycol, and polyurethane. In some embodiments, the hydrogel is comprised of alginate.

The Micro-Organospheres described herein may also include biologically-relevant materials. The phrase "biologically-relevant materials" may describe materials that are capable of being included in a biocompatible medium as defined herein and subsequently interacting with and/or influencing biological systems. For example, in some implementations, the biologically-relevant materials are magnetic beads (i.e., beads that are magnetic themselves or that contain a material that responds to a magnetic field, such as iron particles) that can be combined as part of the unpolymerized material to produce Micro-Organosphere that can be used in the methods and compositions (e.g., for the separation and purification of Micro-Organospheres). As another example, in other implementations, the biologically-relevant materials may include additional cells, in addition to the dissociated tissue sample (e.g., biopsy) material. In the unpolymerized mixture the dissociated tissue sample and the additional biologically relevant material in a uniform mixture or as a distributed mixture (e.g., on just one half or other portion of the Micro-Organosphere, including just in the core or just in the outer region of the formed Micro-Organosphere). In some variations the additional biologically-relevant material within the unpolymerized material may be suspended with the dissociated tissue sample in suspension, e.g., prior to polymerization of the droplet forming the Micro-Organosphere.

In some variations the biologically relevant material that may be included with the dissociated tissue sample (e.g., biopsy) material may contain a number of cell types, including preadipocytes, mesenchymal stem cells (MSCs), endothelial progenitor cells, T cells, B cells, mast cells, and adipose tissue macrophages, as well as small blood vessels or microvascular fragments found within the stromal vascular fraction.

In general, with respect to the dissociated tissue sample, e.g., biopsy, material that is included in the Micro-Organospheres described herein, these tissues may be any appropriate tissue from a patient, typically taken by biopsy. Although non-biopsy tissue may be used, in general, these tissues (and the resulting dissociated cells) may be primary cell taken from a patient biopsy as described above, e.g., by a needle biopsy. Tissues may be from a healthy tissue biopsy or from cancerous (e.g., tumor) cell biopsy. The dissociated cells may be incorporated into a Micro-Organosphere of the presently-disclosed subject matter, based on the intended use of that Micro-Organosphere. For example, relevant tissues (e.g., dissociated biopsy tissue) may typically include cells that are commonly found in that tissue or organ (or tumor, etc.). In that regard, exemplary relevant cells that can be incorporated into Micro-Organosphere of the presently-disclosed subject matter include neurons, cardiomyocytes, myocytes, chondrocytes, pancreatic acinar cells, islets of Langerhans, osteocytes, hepatocytes, Kupffer cells, fibroblasts, myoblasts, satellite cells, endothelial cells, adipocytes, preadipocytes, biliary epithelial cells, and the like. These types of tissues may be dissociated by conventional techniques known in the art. Suitable biopsied tissue can be derived from: bone marrow, skin, cartilage, tendon, bone, muscle (including cardiac muscle), blood vessels, corneal, neural, brain, gastrointestinal, renal, liver, pancreatic (including islet cells), lung, pituitary, thyroid, adrenal, lymphatic, salivary, ovarian, testicular, cervical, bladder, endometrial, prostate, vulval and esophageal tissue. Normal or diseased (e.g., cancerous) tissue may be used. In some variations, the tissue may arise from tumor tissue, including tumors originating in any of these normal tissues.

Once formed the Micro-Organospheres may be cryopreserved and/or cultured. Cultured Micro-Organospheres may be maintained in suspension, either static (e.g., in a well, vial, etc.) or in motion (e.g., rolling or agitated). The Micro-Organosphere may be cultured using known culturing techniques. Exemplary techniques can be found in, among other places;

Freshney, Culture of Animal Cells, A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559,022.

In some variations the Micro-Organospheres are formed by forming a droplet of the unpolymerized mixture (e.g., in some variations a chilled mixture) of a dissociated tissue sample and a fluid matrix material in an immiscible material, such as a fluid hydrophobic material (e.g., oil). For example, a Micro-Organosphere may be formed by combining a stream of unpolymerized material with one or more streams of the immiscible material to form a droplet. The density of the cells present in the droplet may be determined by the dilution of the dissociated material (e.g., cells) in the unpolymerized material. The size of the Micro-Organosphere may correlate to the size of the droplet formed. In general, the Micro-Organosphere is a spherical structure having a stable geometry.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

As used herein a drug composition may include any drug, drug dilution, drug formulation, compositions including multiple drugs (e.g., multiple active ingredients), drug formulations, drug forms, drug concentrations, combination therapies, and the like. In some variations a drug formulation refers to a formulation comprising a mixture of a drug and one or more inactive ingredients.

As used here the term "passaged" may refer to the average number of doublings of the cells within the Micro-Organospheres. Although traditional passage number refers to the transfer or subculture of cells from one culture vessel to another, the cells within a Micro-Organospheres may be stably retained within the same Micro-Organospheres, and may continue to grow and divide. Thus, the passage number as used herein typically refers to the average number of doublings undergone by the dissociated cells from the biopsied tissue within the Micro-Organospheres. The population doubling number is the approximate number of doublings that the cell population has undergone since isolation (e.g., since forming of the Micro-Organospheres from the freshly dissociated biopsy tissue). In general, the Micro-Organospheres described herein may be cultured for a short period of time relative to the growth, e.g., doublings, of some or all of cells within the Micro-Organospheres (e.g., fewer than 10 passages, fewer than 9 passages, fewer than 8 passages, fewer than 7 passages, fewer than 6 passages, fewer than 5 passages, fewer than 4 passages, fewer than 3 passages, etc.).

During culturing, the cells from the dissociated, biopsied tissue in the Micro-Organospheres can aggregate, cluster or assemble within the Micro-Organospheres. Aggregates of cells may be highly organized, and may form defined morphology or may be a mass of cells that have clustered or adhered together. The organization may reflecting the tissue of origin. Although in some variations the Micro-Organospheres may contain a single cell type (homotypic), more typically these Micro-Organospheres may contain more than one cell type (heterotypic).

As mentioned, the (e.g., biopsy) tissue used to form the Patient-Derived Micro-Organospheres (e.g., the dissociated tissue) may be derived from a normal or healthy biological tissue, or from a biological tissue afflicted with a disease or illness, such as a tissue or fluid derived from a tumor. The tissue used in the Micro-Organospheres may include cells of the immune system, such as T lymphocytes, B lymphocytes, polymorphonuclear leukocytes, macrophages and dendritic cells. The cells may be stem cells, progenitor cells or somatic cells. The tissue may be mammalian cells such as human cells or cells from animals such as mice, rats, rabbits, and the like.

In general, these tissue (and resulting cells) may generally be taken from a biopsy to form the Micro-Organospheres. Thus, the tissue may be derived from any of a biopsy, a surgical specimen, an aspiration, a drainage, or a cell-containing fluid. Suitable cell-containing fluids include any of blood, lymph, sebaceous fluid, urine, cerebrospinal fluid or peritoneal fluid. For example, in patients with transcoelomic metastasis, ovarian or colon cancer cells may be isolated from peritoneal fluid. Similarly, in patients with cervical cancer, cervical cancer cells may be taken from the cervix, for example by large excision of the transformation zone or by cone biopsy. Typically, such Micro-Organospheres will contain multiple cell types that are resident in the tissue or fluid of origin. The cells may be obtained directly from the subject without intermediate steps of subculture, or they may first undergo an intermediate culturing step to produce a primary culture. Methods for harvesting cells from biological tissue and/or cell containing fluids are well known in the art. For example, techniques used to obtain cells from biological tissue include those described by R. Mahesparan (Extracellular matrix-induced cell migration from glioblastoma biopsy specimens in vitro. Acta Neuropathol (1999) 97:231-239).

Generally, the cells are first dissociated or separated from each other before forming the Micro-Organospheres. Dissociation of cells may be accomplished by any conventional means known in the art. Preferably, the cells are treated mechanically and/or chemically, such as by treatment with enzymes. By 'mechanically' we include the meaning of disrupting connections between associated cells, for example, using a scalpel or scissors or by using a machine such as an homogenizer. By 'enzymatically' we include the meaning of treating the cells with one or more enzymes disrupt connections between associated cells, including for example any of collagenase, dispases, DNAse and/or hyaluronidase. One or more enzymes may be used under different reaction conditions, such as incubation at 37° C. in a water bath or at room temperature.

The dissociated tissue may be treated to remove dead and/or dying cells and/or cell debris. The removal of such dead and/or dying cells may be accomplished by any conventional means known to those skilled in the art, for example using beads and/or antibody methods. It is known, for example, that phosphatidylserine is redistributed from the inner to outer plasma membrane leaflet in apoptotic or dead cells. The use of Annexin V-Biotin binding followed by binding of the biotin to streptavidin magnetic beads enables the separation of apoptotic cells from living cells. Similarly, removal of cell debris may be achieved by any suitable technique in the art, including, for example, filtration.

The dissociated cells may be suspended in a carrier material prior to combining with the fluid matrix material, and/or the fluid matrix material may be referred to as a carrier material. In some variations the carrier material may be a material that has a viscosity level that delays sedimentation of cells in a cell suspension prior to polymerization and formation of the Micro-Organospheres. A carrier material may have sufficient viscosity to allow the dissociated biopsy tissue cells to remain suspended in the suspension until polymerization. The viscosity required to achieve this can be optimized by the skilled person by monitoring the sedimentation rate at various viscosities and selecting a viscosity that gives an appropriate sedimentation rate for the expected time delay between loading the cell suspension into the apparatus forming the Micro-Organospheres forming the Micro-Organospheres by polymerizing the droplets of the unpolymerized material including the cells. In some variations the unpolymerized material may be flowed or agitated by the apparatus even where lower viscosity materials are used, in order to keep the cells in suspension and/or distributed as desired.

As mentioned above, in some variations the unpolymerized mixture, including the dissociated tissue sample and the fluid matrix material may include one or more components, e.g., biologically-relevant materials. For example, a biologically-relevant material that may be included may include any of: an extracellular matrix protein (e.g. fibronectin), a drug (e.g. small molecules), a peptide, or an antibody (e.g., to modulate any of cell survival, proliferation or differentiation); and/or an inhibitor of a particular cellular function. Such biologically-relevant materials may be used, for example, to increase cell viability by reducing cell death and/or activation of cell growth/replication or to otherwise mimic the in vivo environment. The biologically-relevant materials may include or may mimic one or more of the following components: serum, interleukins, chemokines, growth factors, glucose, physiological salts, amino acids and hormones. For example, the biologically-relevant materials may supplement one or more agents in the fluid matrix material. In some variations, the fluid matrix material is a synthetic gel (hydrogel) and may be supplemented by one or more biologically-relevant materials. In some variations the fluid matrix is a natural gel. Thus, the gel may be comprised of one or more extracellular matrix components such as any of collagen, fibrinogen, laminin, fibronectin, vitronectin, hyaluronic acid, fibrin, alginate, agarose and chitosan. For example, MATRIGEL comprises bioactive polymers that are important for cell viability, proliferation, development and migration. For example, the matrix material may be a gel that comprises collagen type 1 such as collagen type 1 obtained from rat tails. The gel may be a pure collagen type 1 gel or may be one that contains collagen type 1 in addition to other components, such as other extracellular matrix proteins. A synthetic gel may refer to a gel that does not naturally occur in nature. Examples of synthetic gels include gels derived from any of polyethylene glycol (PEG), polyhydroxyethyl methacrylate (PHEMA), polyvinyl alcohol (PVA), poly ethylene oxide (PEO).

Patient-Derived Micro-Organospheres

Figure 1B:
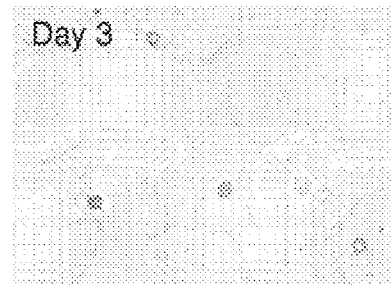
Figure 1C:
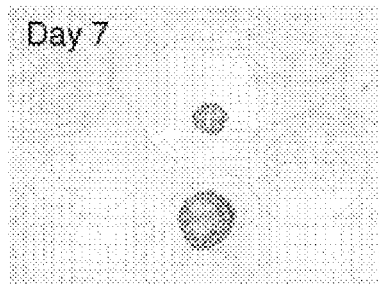
Figure 2A:
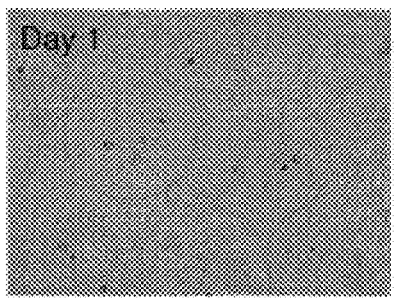
FIGS. 2A to 2C illustrate Patient-Derived Micro-Organospheres formed as described herein to include five dissociated primary tissue cells per Micro-Organosphere, cultured for one day after forming (FIG. 2A), cultured for three days after forming (FIG. 2B), and cultured for seven days after forming (FIG. 2C). The cells originate from colorectal cancer (CRC) tissue.
Figure 2B:
Figure 2C:
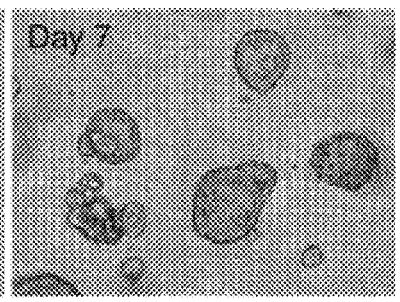
Figure 3A:
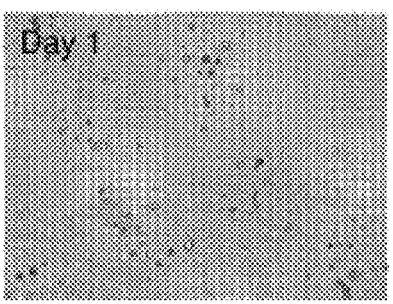
FIGS. 3A to 3C illustrate Patient-Derived Micro-Organospheres formed as described herein to include twenty dissociated primary tissue cells per Micro-Organosphere, cultured for one day after forming (FIG. 3A), cultured for three days after forming (FIG. 3B), and cultured for seven days after forming (FIG. 3C). As in FIGS. 1A-1C and 2A-2C, the cells originate from colorectal cancer (CRC) tissue.
Figure 3B:
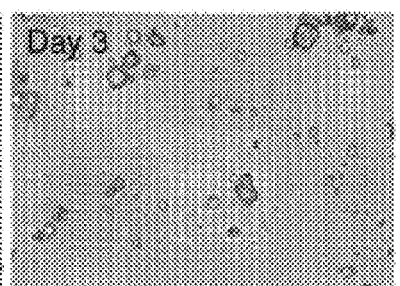
Figure 3C:
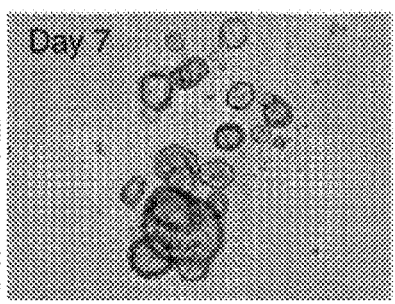

Examples of Patient-Derived Micro-Organospheres are shown in FIGS. 1A-1C, 2A-2C, 3A-3C and 4A-4E. For example, FIGS. 1A-1C illustrate Micro-Organospheres formed having a single cell per Micro-Organosphere. As shown, the Micro-Organospheres are all approximately the same size, e.g., approximately 300 µm diameter. FIG. 1B shows Micro-Organospheres formed at the same time after 3 days in culture. The cells have expanded in size, in some cases doubling and/or growing. By seven days in culture, as shown in FIG. 1C, the cells have doubled multiple times, showing clusters or masses of cells.

Figure 4A:
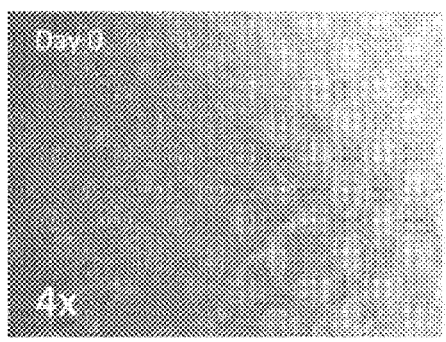
FIGS. 4A to 4E illustrate examples of Patient-Derived Micro-Organospheres formed as described herein to include ten dissociated primary tissue cells per Micro-Organosphere.
Figure 4B:
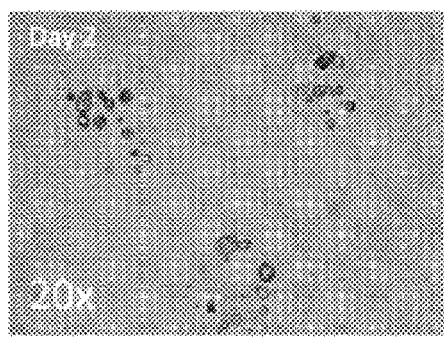
Figure 4C:
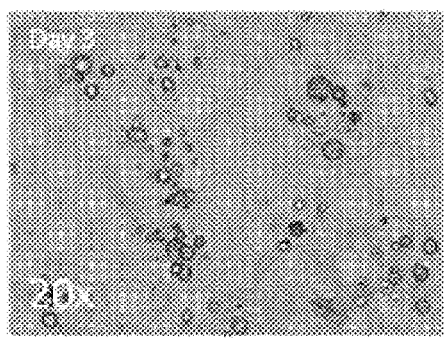
Figure 4D:
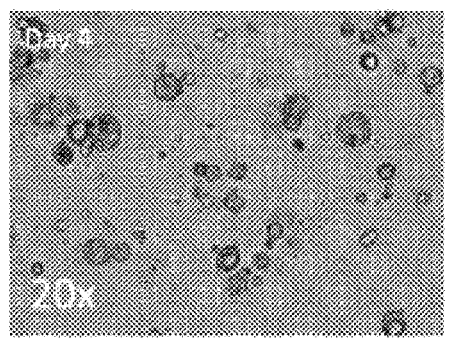
Figure 4E:
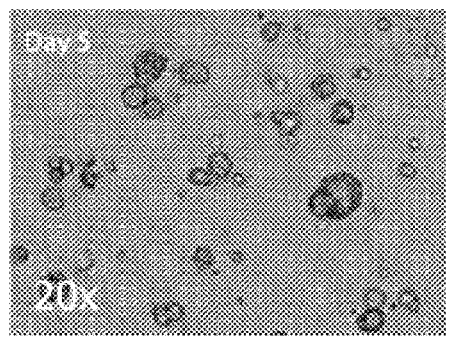

Similar results are shown in FIGS. 2A-2C and 3A-3C showing Micro-Organospheres formed from five cells per Micro-Organosphere or 20 cells per Micro-Organospheres, respectively. In FIGS. 4A-4E, the Micro-Organospheres are shown immediately after formation, and cultured for five days, in which nearly-identical Micro-Organospheres (e.g., having the same diameter) each include 10 cells per Micro-Organosphere. In FIG. 4A, the Micro-Organospheres are shown immediately after forming, still surrounded by the immiscible fluid, in this case, oil, at day 0. The Micro-Organospheres are removed from the immiscible fluid and washed, and cultured for five days. FIG. 4B shows the Micro-Organospheres after 2 days, FIG. 4C shows the Micro-Organospheres after 3 days, and FIGS. 4D and 4E show the Micro-Organospheres at 4 and 5 days, respectively. FIGS. 4A-4E show that the dissociated tissue (cells) from the biopsy within the Micro-Organospheres are viable and growing within nearly all of the Micro-Organospheres at comparable rates. As will be described in greater detail there, these Micro-Organospheres may be formed in large amounts from even a single, average-sized biopsy and may result in many hundreds or thousands (e.g., 500, 750, 1000, 2000, 5000, 10,000 or more) of Micro-Organospheres that include a significant number of viable cells, allowing multiple rapid assays to be performed in parallel.

Figure 5A:
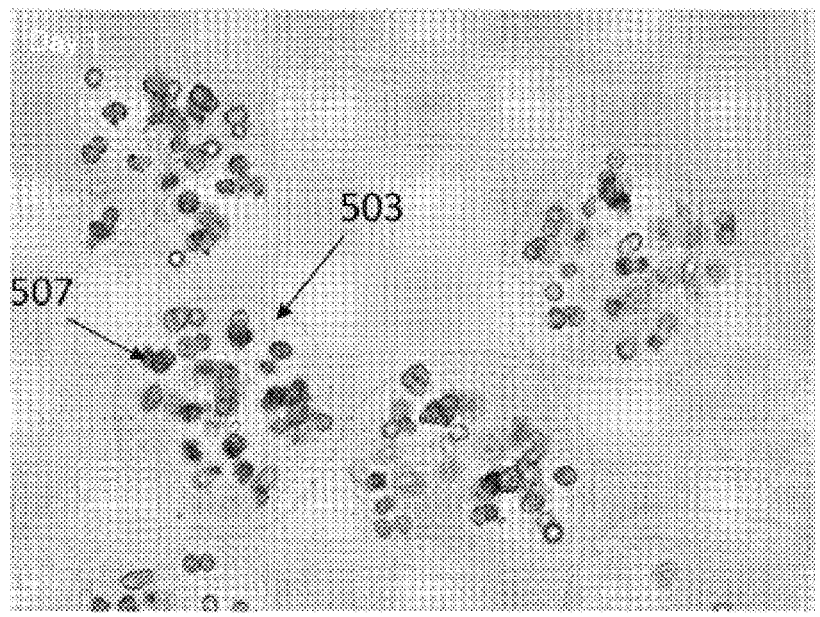
FIGS. 5A to 5B illustrate examples of Micro-Organospheres formed as described herein from normal mouse liver hepatocytes, cultured for one day after forming (FIG. 1A), cultured for ten days after forming (FIG. 1B), The mouse hepatocytes are taken from a normal (e.g., non-diseased) mouse liver.
Figure 5B:
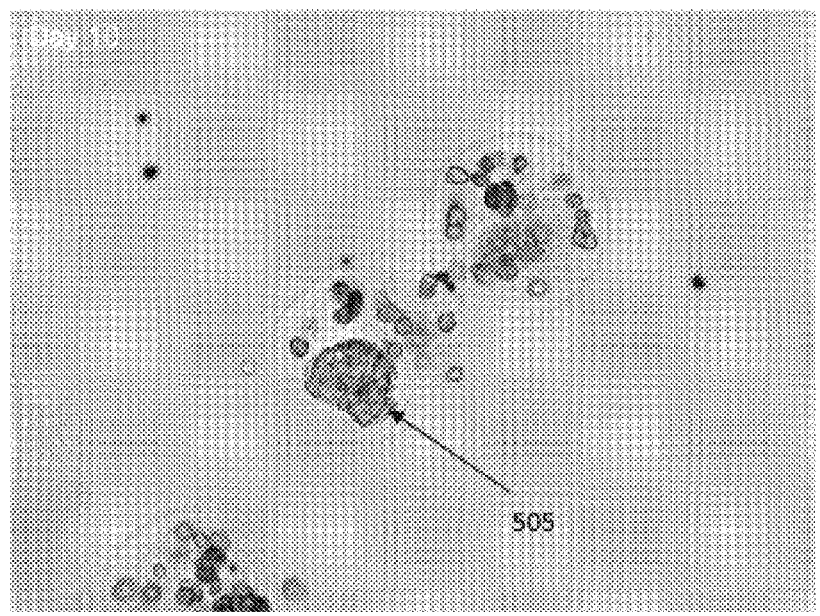

FIGS. 5A and 5B illustrate an example of Micro-Organospheres formed as described herein from a dissociated biopsy of mouse liver, e.g., showing mouse hepatocytes distributed within a polymerized fluid matrix material (in this example, MATRIGEL). Each Micro-Organospheres includes the polymerized matrix material 503 formed into a sphere having a diameter, e.g., of about 300 µm, in which a set number of hepatocytes 507 are dispersed. In FIG. 5A, the Micro-Organospheres are shown one day after biopsying, dissociation and forming of the Micro-Organospheres. These Micro-Organospheres were then cultured for 10 days, during which time the cells (hepatocytes) remained viable and grew, in many cases doubling multiple times to form structures 505, as shown in FIG. 5B.

The Micro-Organospheres may generally include the dissociated, e.g. biopsy, tissue (e.g., cells) in a fixed or known number of cells and/or concentration (cells/ml or cells/mm$^3$) within the Micro-Organospheres. As mentioned above, this matrix material may be natural polymers, such as one or more of: alginate, agarose, hyaluronic acid, collagen, gelatin, fibrin, elastin; or a synthetic polymer, such as one or more of: polyethylene glycol (PEG) and polyacrylamide. Both organic and inorganic synthetic polymers may be used.

In some variations the number of cells initially included in the Micro-Organospheres may be selected from between 1 cell up to several hundred. In particular, in some assays (e.g., drug toxicity assays) it may be beneficial to include between about 1-75 or between about 1-50 (e.g., lower numbers of cells). The number of cells per Micro-Organosphere may be set or selected by the user. In some variations, as described below, the apparatus will include one or more controls to set the number of cells from the primary tissue to include in each Micro-Organosphere. The number of cells may be chosen or set based on how the user intends to use the Micro-Organospheres. For example, Micro-Organospheres having very low number of cells (e.g., 1 cell per Micro-Organosphere, 1-5 cells per Micro-Organosphere, etc.) may be particularly suitable for studying clonal diversity (e.g., for tumor heterogeneity). Since each Micro-Organosphere grows from a single cell, we can observe which clones are drug resistant and these specific Micro-Organospheres may be examined (e.g., by genomic sequencing) to determine the genomic (mutation) diversity related to the particular clone. A low to moderate number of cells per Micro-Organosphere (e.g., between about 3-30 cells, 5-30 cells, 5-25 cells, 5-20 cells, 10-25 cells, etc.) may be particularly useful for rapid drug testing, including toxicity testing as these Micro-Organospheres typically grow quickly. A larger number of cells per Micro-Organosphere (e.g., between about 20-100 cells, e.g., 30-100 cells, 40-100 cells, greater than 50 cells, etc.) may be particularly suitable for mimicking tissue composition in each Micro-Organosphere, as the Micro-Organosphere may contain different lineages, potentially including epithelial (or cancer, etc.) and mesenchymal (or stromal, immune, blood vessel, etc.) cells.

The Micro-Organospheres may be formed in any appropriate size, which may be matched to the number of cells to be included. For example, the size may be as small as about 20 µm, up to 500 µm in diameter (e.g., 50 or 100 µm on average, e.g., between about 100-200 µm, etc.). In some variations the size is about 300 µm in which between about 10-50 cells (e.g., between about 10-30 cells) are included in each Micro-Organosphere. The number of cells and the size may be varied and/or may be controlled. In some variations the number of cells and/or the size of the Micro-Organospheres may be set by one or more controls on the apparatus forming the Micro-Organospheres. For example, the size of the Micro-Organospheres and/or the density of cells within the Micro-Organospheres may be adjusted by adjusting the flow rates and/or the concentration of the dissociated tissue sample (e.g., the cells from a biopsy).

As shown in FIGS. 1A-5B, even after culturing the Micro-Organospheres described herein allow for viable and healthy cells through the entire volume of the Micro-Organosphere. The size of the Micro-Organospheres and/or the number of cells to be included in the Micro-Organospheres may be selected based on how the Micro-Organospheres are expected or intended to be used. For example, in variations in which the Micro-Organospheres is to be used to examine relationships between cells of the biopsied material the Micro-Organospheres may be formed having multiple cells and may be cultured for extended periods of time (e.g., up to one week or more).

Figure 6:
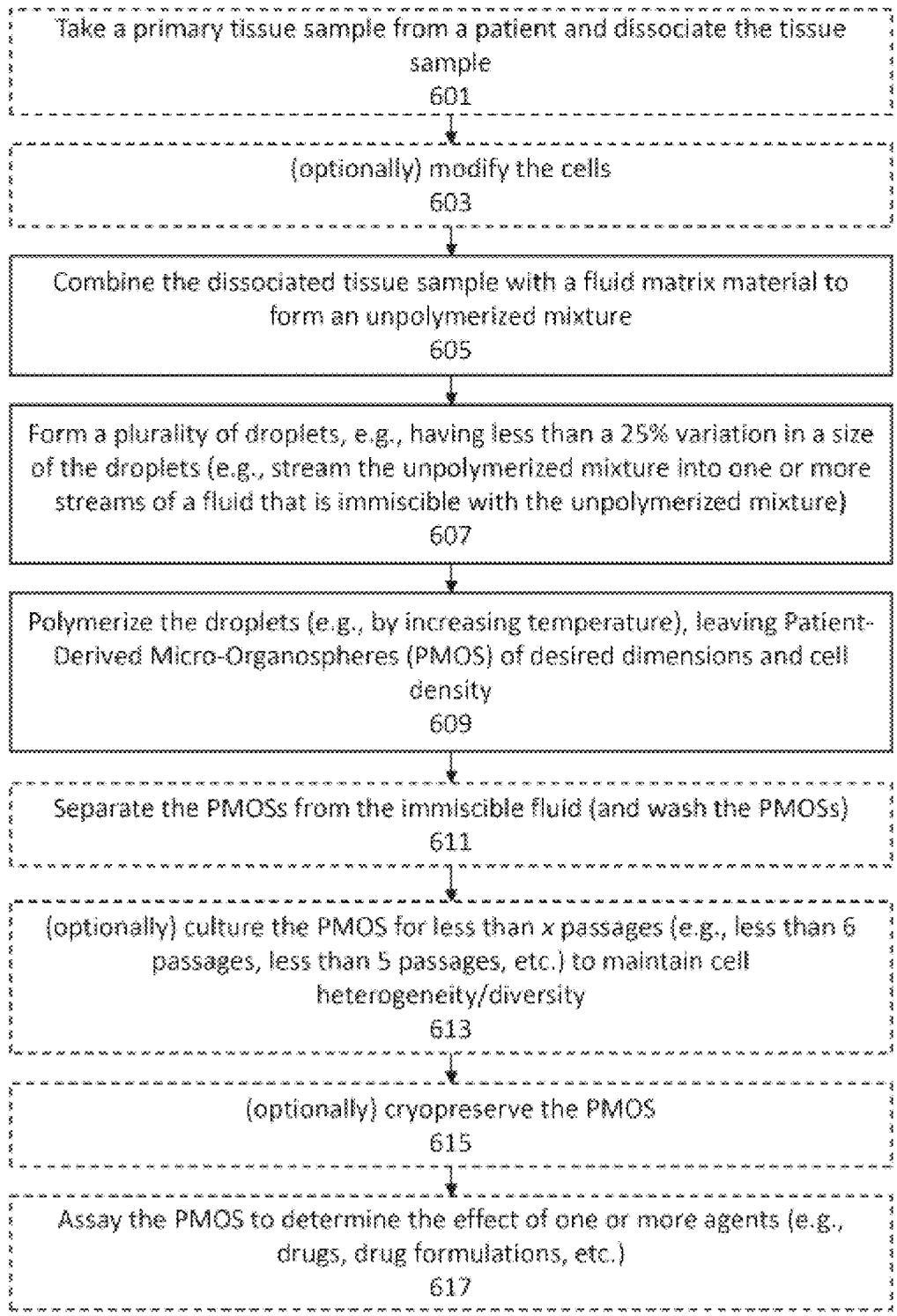
FIG. 6 illustrates on the method of forming Patient-Derived Micro-Organospheres from primary tissue (e.g., biopsy) samples, as described herein.

The Patient-Derived Micro-Organospheres described herein may be made by combining a dissociated tissue sample, e.g., a biopsy sample, with a fluid matrix that may be polymerized in a controlled manner to form the Micro-Organospheres. FIG. 6 illustrates one method of forming Patient-Derived Micro-Organospheres. Optionally, the method may include taking the sample from a patient, such as taking a biopsy from a patient tissue 601. As mentioned above, the biopsy may be taken, e.g., using a biopsy needle or punch. For example, the biopsy may be taken with a 14-gauge, a 16-gauge, an 18-gauge, etc. needle that is inserted into the patient tissue to remove the biopsy. After removing the tissue from the patient, the tissue may be processed to dissociate the material, either mechanically and/or chemically. The dissociated cells may be immediately used to form the Patient-Derived Micro-Organospheres, as described; in some variations, all or some of the cells may be modified, such as by genetically modifying the cells 603, for example, by transfection, electroporation, etc.

The dissociated tissue sample from the biopsy material may be combined with the fluid (e.g., liquid) matrix material to form the unpolymerized mixture 605. This unpolymerized mixture may be held in an unpolymerized state, so that the cells from the dissociated tissue may remain suspended within the mixture. In some variations the cell may remain suspected and unpolymerized by keeping them chilled, e.g., at room temperature of below (e.g., between 1-25 degrees C.).

The unpolymerized mixture may then be dispensed as droplets, e.g., into an immiscible material, such as an oil, in a manner that controls the formation of the size of the droplets and therefore the size of the Patient-Derived Micro-Organospheres formed 607. For example, uniformly-sized droplets may be formed by combining a stream of the unpolymerized material into one or more (e.g., two converging) streams of the immiscible material (e.g., oil) so that the flow rates and/or pressures of the two streams may determine how droplets of the unpolymerized material are formed as they intersect the immiscible material. The droplets may be polymerized 609 to form the Patient-Derived Micro-Organospheres (PMOSs) in the immiscible material. In some variations the immiscible material may be heated or warmed to a temperature that causes the unpolymerized mixture (e.g., the fluid matrix material in the unpolymerized material) to polymerize. Once formed, the Patient-Derived Micro-Organospheres may be separated from the immiscible fluid, e.g., the PMOSs may be washed to remove the immiscible fluid 611, and placed in a culture media to allow the cells within the Patient-Derived Micro-Organospheres to grow. The Patient-Derived Micro-Organospheres may be cultured for any desired time, or may be cryopreserved and/or assayed immediately. In some variations the Patient-Derived Micro-Organospheres may be cultured for a brief period of time (e.g., for between 1-3 days, between 1-4 days, between 1-5 days, between 1-6 days, between 1-7 days, between 1-8 days, between 1-9 days, between 1-10 days, between 1-11 days, between 1-14 days etc.). This may allow the cells derived from the dissociated biopsy tissue to grow and/or divide (e.g., double) for up to five or six passages. After culturing, the cells may be either or both cryopreserved 615 and/or assayed 617. Examples of assays that may be used are also described herein.

In any of these methods and apparatuses described herein, the Micro-Organospheres may be recovered from the immiscible fluid (e.g., oil) after polymerization. For example, in some variations, the Micro-Organospheres may be recovered by demulsficiation and/or de- emulsification, for example, by forming emulsified droplets and recovering the Micro-Organospheres after the droplets are formed to remove any oil (and other contaminants). This may allow the cells to grow within the polymerized droplet (the Micro-Organosphere) without being inhibited by the immiscible fluid.

Although the methods and apparatuses described herein illustrate methods of forming the plurality of droplets, and thus the plurality of Micro-Organospheres, by streaming the unpolymerized mixture into one or more streams of immiscible fluid (such as an oil or other hydrophobic material), ins some variations the droplets may be formed by other methods that may allow for the size of the droplet to be controlled as described herein. For example in some variations the droplets may be formed by printing (e.g., by printing droplets onto a surface). This may reduce or eliminate the need for an additional recovery step of emulsification/de-emulsification. For example, the droplets may be printed onto a surface, such as a flat or shaped surface, and polymerized. In any of these variations, the droplets may be dispensed using pressure, sound, charge, etc. In some variations, the droplets may be formed using an automatic dispenser (e.g., pipetting device) adapted to release the small amount of the unpolymerized mixture onto a surface, into the air, and/or into a liquid medium (including an immiscible fluid).

The method for forming the Patient-Derived Micro-Organospheres may be automated, or performing using one or more apparatuses. In particular, the method of forming the Patient-Derived Micro-Organospheres may be performed by an apparatus that allows the selection and/or control of the size of the Patient-Derived Micro-Organospheres (and therefore the density of the number of cells). For example, FIG. 7A illustrates one example of an apparatus 700 for forming Patient-Derived Micro-Organospheres as described.

Figure 7A:
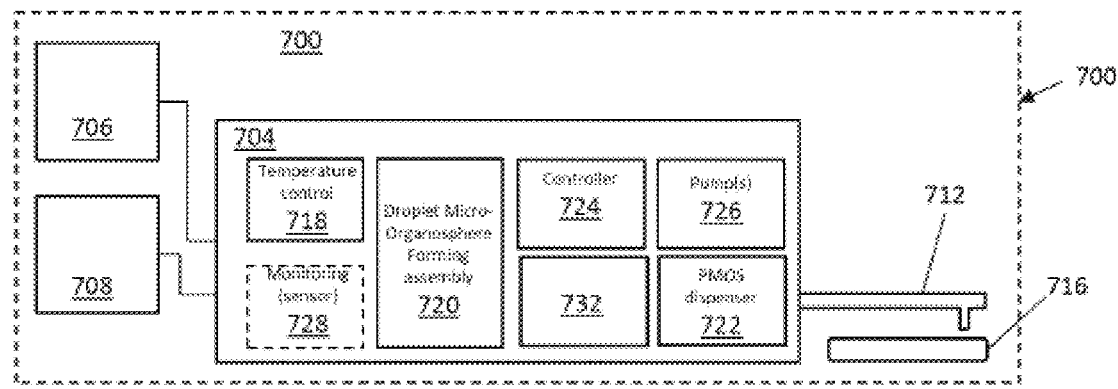
FIG. 7A schematically illustrates one example of an apparatus for forming Patient-Derived Micro-Organospheres as described herein, including a microfluidic chip as part of the assembly.

In FIG. 7A, the apparatus typically includes an input for inputting either the unpolymerized mixture of the dissociated tissue sample and a fluid matrix material (already combined) or may separately receive the dissociated tissue sample, e.g., in a holding solution, and a fluid matrix material. In some variations the apparatus include a holding chamber 706 for holding the unpolymerized mixture, and/or holding chambers (not shown) for holding the dissociated tissue (e.g., biopsy) sample and holding the fluid matrix material. Any or all of these holding chambers may be pressurized to control and/or speed up fluid flow out of the chambers and into the device. The apparatus may either receive the unpolymerized mixture or it may receive the components and mix it. In some variations the apparatus may control the concentration of the cells in the unpolymerized mixture and may dilute the mixture (e.g., by adding additional fluid matrix material to achieve a desired density. For example, the apparatus may include a sensor (e.g., an optical reader) for reading the density (e.g., the optical density) of the cells in the unpolymerized mixture (not shown). The sensor may also be coupled to the controller 724, which may automatically or semi-automatically (e.g., by indicating to a user) control the dilution of the cells in the unpolymerized mixture. The apparatuses may also include a port for receiving the unpolymerized mixture. The port may include a valve or may be coupled to a valve and the valve may be controlled by the controller 724 (or a separate controller).

The apparatus 700 may include a chamber 708 and/or port for holding and/or receiving the immiscible fluid. In some variations the immiscible fluid may be held in a pressurized chamber so that the flow rate may be controlled. Any of the pressurized chambers may be controlled by the controller 724 which may use one or more pumps 726 to control the pressure and therefore the flow through the apparatus. One or more pressure and/or flow sensors may be included in the system to monitor the flow through the device.

In FIG. 7A, the entire apparatus 700 may be enclosed in a housing 702 or a portion of the apparatus 704 may be enclosed in a housing. In some variations the housing may include one or more openings or access portions on the device, e.g., for adding the immiscible fluid and/or the unpolymerized mixture.

As mentioned, any of these apparatuses 700 may also include one or more sensors 728 for monitoring all or key portions of the manufacturing process. In some variations, the sensors may include optical sensors, mechanical sensors, voltage and/or resistance (or capacitance, or inductance) sensors, force sensors, etc. These sensors may be used to monitor the ongoing operation of the assembly, including the formation of the Patient-Derived Micro-Organospheres. The apparatus 700 may also include one or more thermal/temperature regulators 718 for controlling the temperatures of either or both the immiscible fluid and/or the unpolymerized mixture (and/or the fluid matrix material).

Any of these apparatuses may also include one or more droplet forming assemblies 720 that may be monitored (e.g., using one or more sensors) as will be illustrated below in FIGS. 7C and 9. The droplet Micro-Organosphere forming assembly may include (or may be coupled with, a dispenser (e.g., a PMOS dispenser) 722. The dispenser may dispense, for example, in to a multi-well plate 716.

Figure 7B:
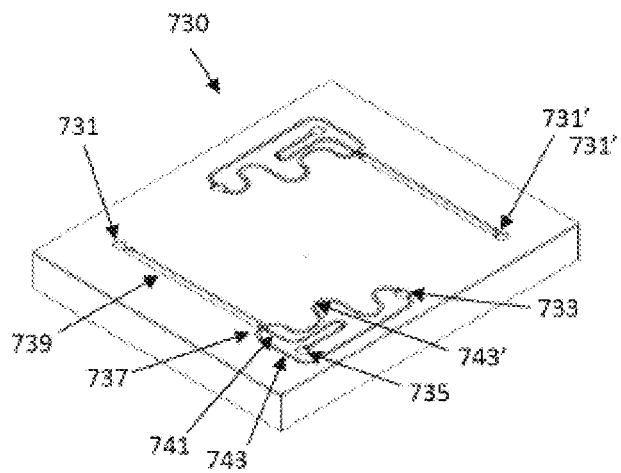
FIG. 7B is a perspective view of one example a microfluidics chip portion of an apparatus such as that shown in FIG. 7A.

In general the droplet Micro-Organosphere forming assembly 720 may include one or more microfluidic chips 730 or structures that forms and controls the streams of the unpolymerized mixture and forms the actual droplets. FIG. 7B illustrates one example of a microfluidic chip for forming Patient-Derived Micro-Organospheres 730. In FIG. 7B, the chip 730 includes a pair of parallel structures for forming Micro-Organospheres. FIG. 7C illustrates the droplet-forming region of the microfluidic chip for forming PMOSs, including an unpolymerized channel outlet 741 that opens (in this example, as a right angle) a "+" junction or region of intersection 737 to the channel outlet 741 and the immiscible fluid outlet(s), 743, 743'. In some variations the input from the immiscible fluid channel(s) may be at an angle relative to the angle (and point of intersection) with the unpolymerized material. In FIG. 7C, as in all figures in this description showing dimensions, the dimensions shown are exemplary only, and are not intended to be limiting, unless they otherwise specify.

In FIG. 7A, the microfluidics chip 730 include an inlet (input port) 733 for the immiscible fluid into the chip (e.g., from the inlet port or storage chamber shown in FIG. 7A). A second inlet port 735 into the chip may be configured to receive the unpolymerized material and transport it down a semi-tortious path to the junction region. Similarly the inlet port for the immiscible fluid, may be securely coupled to the outlet from the immiscible fluid chamber or inlet, described above.

Figure 7C:
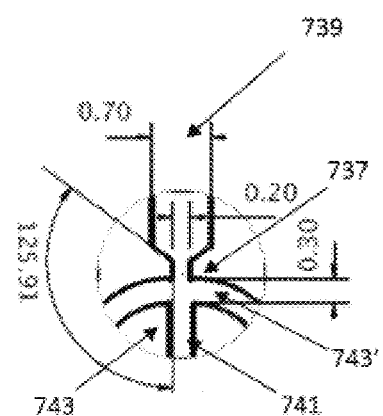
FIG. 7C schematically illustrates a portion of a microfluidics assembly for an apparatus for forming Patient-Derived Micro-Organospheres, such as the one shown in FIG. 7A.

The inlet port 735 for the unpolymerized material into the chip may be coupled through a delivery pathway 741 connecting the inlet 275 to the junction region (as shown in FIG. 7C. Similarly, the inlet 733 for the immiscible fluid may connect to two (or more) connecting paths 743, 743' to the junction region 737. A channel leaving the junction region 737 may pass the formed Micro-Organospheres (in the immiscible fluid) down the channel to an outlet 731 that may connect to a dispenser (not show) for dispensing from the Micro-Organospheres into one or more chambers, e.g., for culture and/or assaying.

In the example shown in FIGS. 7B and 7C the formed droplets, which may become Micro-Organospheres once polymerized, may be transmitted down a long, temperature controlled microfluidics environment, prior to being dispensed from the apparatus (not shown).

For example FIG. 8 illustrates one example of a channel region 839 (e.g., element 739 in FIG. 7B) that is shown transparent, containing a plurality of Micro-Organospheres 803 each containing a predetermined number of cell 805.

In FIG. 8, the junction region 937 is shaped as described above, so that the channel carrying the unpolymerized mixture 911 intersects one or more (e.g., two) channels 909 carrying a fluid, such as an oil, that is immiscible with the unpolymerized mixture. As the unpolymerized mixture is pressurized to flow at first rate out of the first channel 911, the flowing immiscible fluid in the intersecting channels, 909, 909', permit a predefined amount of the unpolymerized mixture to pass before pinching it off to form a droplet 903 that is passed into the outlet channel 939. Thus, in some variations, a minced (e.g., dissociated) clinical (e.g., biopsy or resected) sample of tissue, such as <1 mm in diameter, may be is mixed with a temperature-sensitive gel (i.e. MATRIGEL, at 4 degrees C.) to form the unpolymerized mixture. This unpolymerized mixture may be placed into the microfluidic device that may generates droplets (e.g., water-in-oil droplets) that are uniform in volume and material composition. Simultaneously, the dissociated tumor cells may be partitioned into these droplets. The gel in the unpolymerized material may solidify upon heating (e.g., at 37 degrees C.), and the resulting Patient-Derived Micro-Organospheres may be formed. In some variations this method may be used to produce over 10,000 (e.g., over 20,000, over 30,000, over 40,000, over 50,000, over 60,000, over 70,000, over 80,000, over 90,000, over 100,000) uniform droplets (Patient-Derived Micro-Organospheres) from the tissue (e.g., biopsy material). These Patient-Derived Micro-Organospheres are compatible with traditional 3D cell culture techniques. FIG. 10 illustrates a plurality of Patient-Derived Micro-Organospheres 1005 formed as described above, suspended in the immiscible material 1008 (e.g., oil).

In the exemplary microfluidics chip illustrated above, the junction is shown as a T- or X-junction in which the flow focusing of the microfluidics forms the controllable size of the Micro-Organospheres. In some variations, rather than a microfluidics chip, the droplets may be formed by robotic micro-pipetting, e.g., into an immiscible fluid and/or onto a solid or gel substrate. Alternatively in some variations the droplets of unpolymerized material may be formed in the requisite dimensions and reproducibility by micro-capillary generation. Other example of techniques that may alternatively be used for forming the Micro-Organospheres in the specified size range and reproducibility from the unpolymerized material may include colloid manipulation, e.g., via external forces such as acoustics, magnetics, inertial, electrowetting, or gravitational.

Figure 11A:
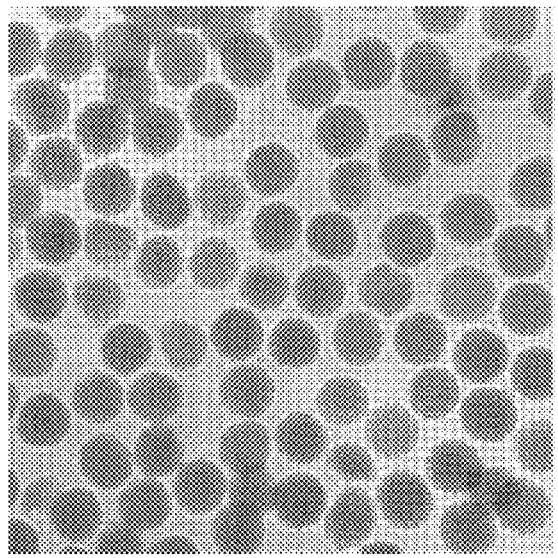
FIGS. 11A-11B illustrate another example of a plurality of Patient-Derived Micro-Organospheres shortly after formation and suspended in the immiscible fluid (e.g., oil) at low magnification (FIG. 11A) and higher magnification (FIG. 11B).
Figure 11B:
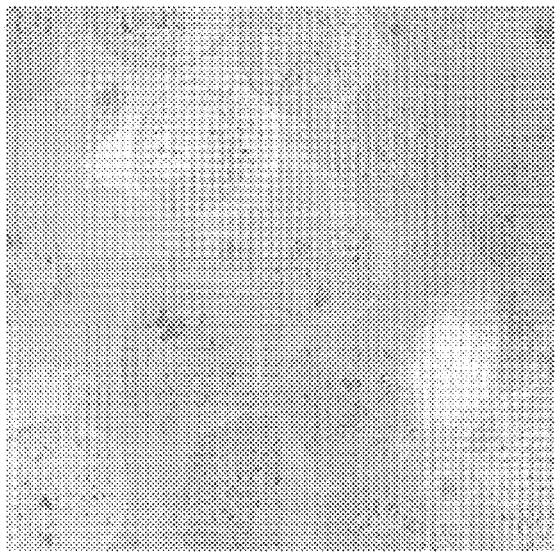
Figure 12A:
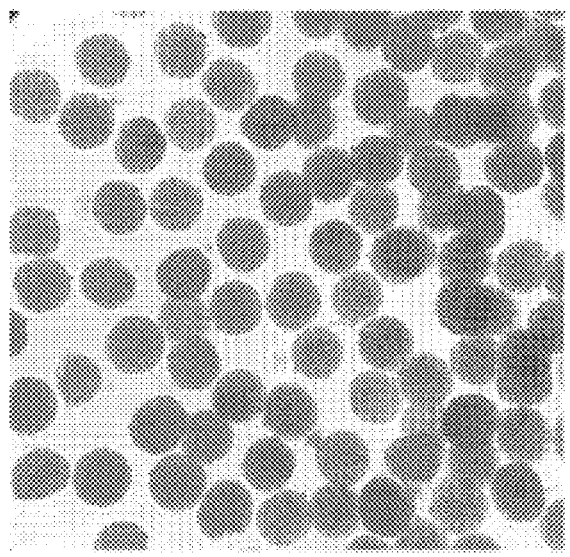
FIGS. 12A-12B show a plurality of Patient-Derived Micro-Organospheres following separation from the immiscible fluid within a few hours of formation of the Patient-Derived Micro-Organospheres at low magnification (FIG. 12A) and higher magnification (FIG. 12B). 100761
Figure 12B:
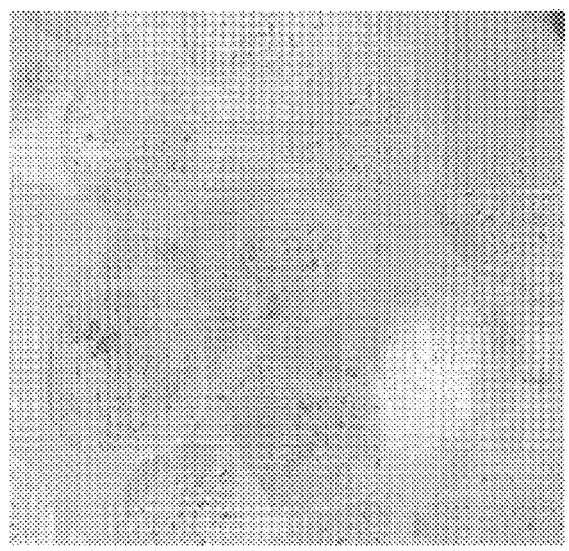

FIGS. 11A and 11B shows examples of Patient-Derived Micro-Organospheres in oil formed as described above. The cells within these Patient-Derived Micro-Organospheres, derived from a single biopsy sample, are viable, as seen by vital dye staining, as shown in FIGS. 15A-15B and 16A-16B. For example, FIG. 12A-12B illustrates Micro-Organospheres having tumor cells (similar to those shown in FIG. 11A-11B) that may be washed to remove the immiscible material (e.g., oil). This immiscible material may be removed relatively quickly after forming the Micro-Organospheres in order to prevent harm to the cells within the Micro-Organosphere.

Figure 13:
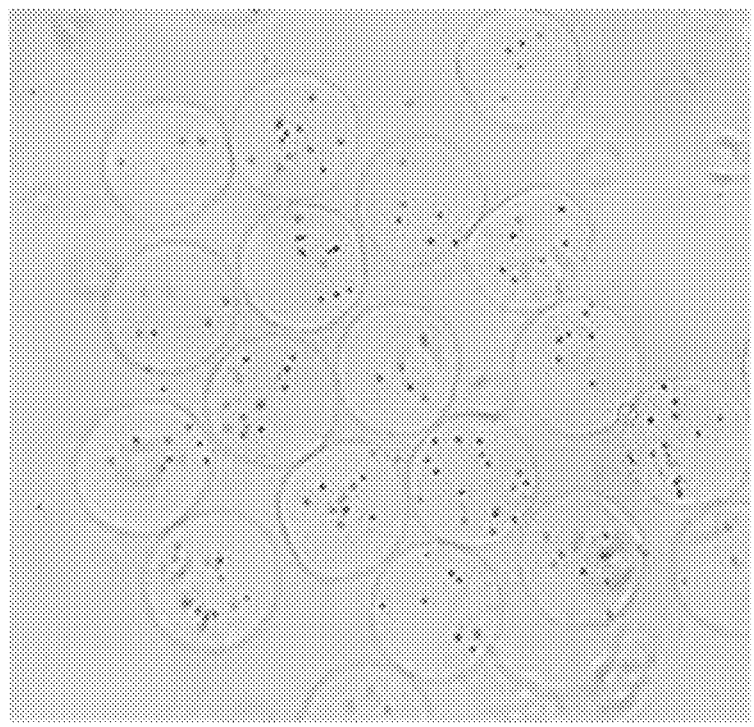
FIG. 13 is another example of an image showing a plurality of Patient-Derived Micro-Organospheres formed as described herein.

In these examples, the gel droplets are recovered from the oil phase and resuspended, e.g., into PBS via PFO (perfluoro octanol) and centrifugation. This may separate the immiscible fluid from the Micro-Organospheres. Thus, these Micro-Organospheres, including tumor-based Micro-Organospheres, can be successfully grown, as shown in FIGS. 1A-1C, 2A-2C, 3A-3C and 4A-4E, above, and in FIG. 13. This is an important improvement, as drug screening has to be performed on viable and growing primary tumor cells that retain their properties from patient tumors to predict patient outcomes. The high number and uniformity of these Micro-Organospheres makes screening both possible and reliable, as will be described below.

In any of the microfluidic chips or devices described herein, the channels may be coated. For example, the channel of the microfluidic device may be coated with a hydrophobic material.

Figure 14:
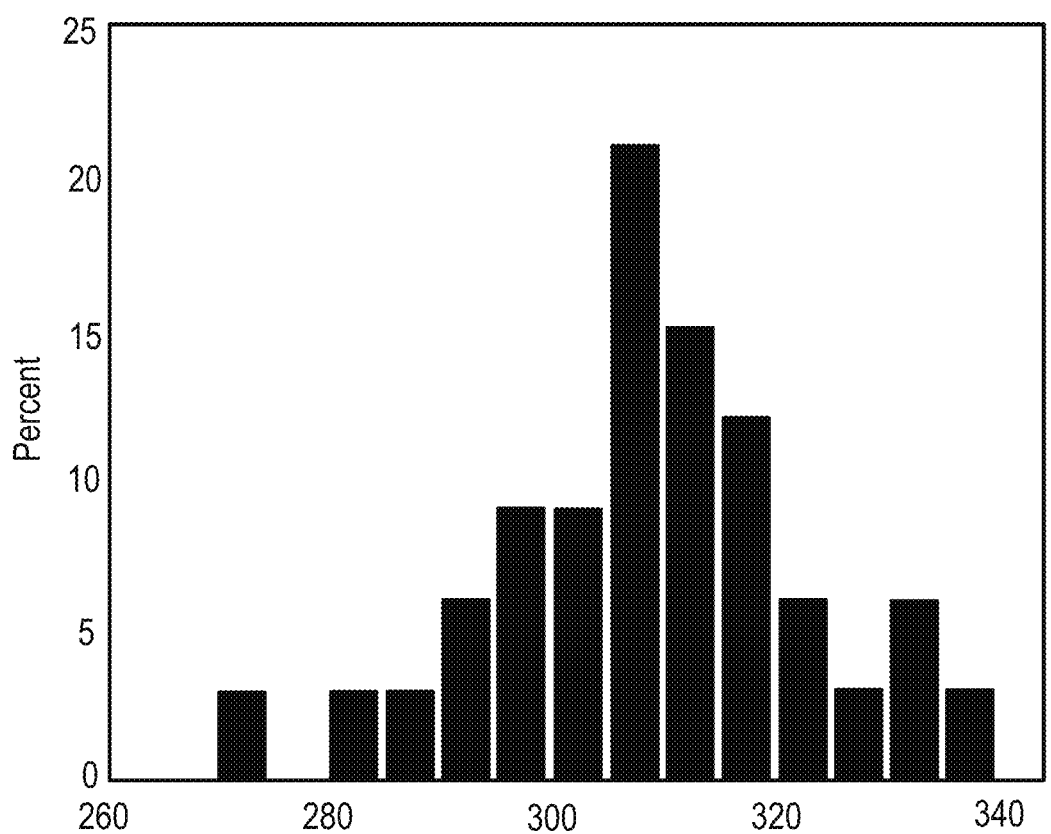
FIG. 14 is a chart illustrating the size distribution of the diameters from a plurality of Patient-Derived Micro-Organospheres formed from an exemplary biopsy sample.

In general, the Micro-Organospheres described herein are highly uniform in diameter, and may have a very low size, e.g., diameter, variance. This is illustrated, for example, in FIG. 14, showing a distribution of one example of droplet diameter sizes.

Figure 15A:
FIGS. 15A-15B illustrate a low and higher magnification views, respectively, of one example of a plurality of Patient-Derived Micro-Organospheres formed from a dissociated tissue biopsy sample and a fluid matrix material, after polymerizing.
Figure 15B:
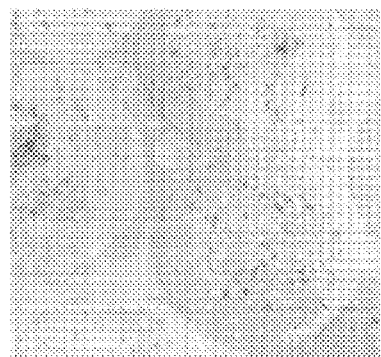
Figure 16A:
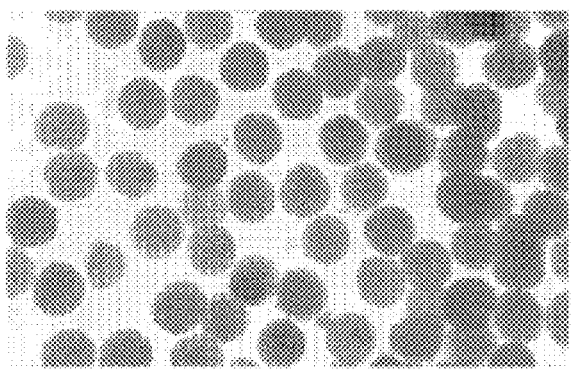
FIGS. 16A-16B is another example, similar to that shown in FIG. 15A-15B, showing low and higher magnification views, respectively, of one example of a plurality of Patient-Derived Micro-Organospheres.
Figure 16B:
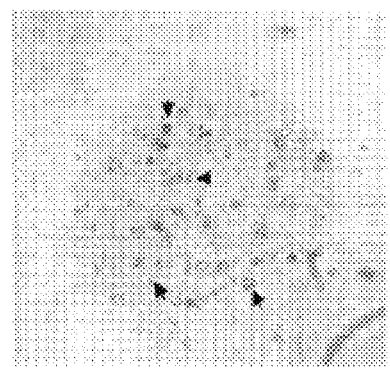

As mentioned, FIGS. 15A-15B shows Micro-Organospheres formed as described herein; in FIG. 16A-16B, these Micro-Organospheres have been stained with Trypan blue (arrowheads), showing that they are alive. The Micro-Organospheres formed as droplets in this manner may contain growth-factors and matrix to mimic the biological environment from which the tissue arose. Patient samples (e.g., biopsy samples) may be formed in to Micro-Organospheres (including hundreds, thousands, or tens of thousands of Micro-Organospheres) within a few hours of acquiring the tissue. The Micro-Organospheres may have as few as 1 or between 4-6 cells (e.g., cancer cells when sampling a tumor) per Micro-Organospheres or as many as hundreds of cells. These methods have been shown to work for virtually all types of cancer and non-cancer tissues tested to date (n=20), including colon, esophagus, melanoma, uterus, sarcoma, renal, liver, ovary, lung, diaphragm, omentum, mediastinal lung, and breast cancer tissues. The Micro-Organospheres may be cultured for any desired period of time, and typically show proliferation and growth in as few as 3-4 days. They may be maintained and passaged for months. As will be described in greater detail below, they may be used to screen thousands of drug compositions within as few as 4-6 days from taking the tissue (e.g., biopsy).

The Micro-Organospheres described herein may, at any point after they are formed, be banked, e.g., by cryopreserving them. Tumor Micro-Organospheres may be collect from many different patients and may be used individual or collectively to screen multiple drug formulations to determine toxicity and/or efficacy. Non-tumorous cells (healthy tissue) may be biopsied, banded and/or screened in parallel. Thus, these methods and apparatuses may allow for high throughput screening. In some variations, the Micro-Organospheres may be formed and allowed to passage twice (e.g., two doublings), and cryopreserved. As mentioned normal, healthy tissue may be use to form these same Micro-Organospheres to generate hundreds, thousands, or tens of thousands of Micro-Organospheres that may be used for assaying drug effects, drug response, biomarkers, proteoimic signals, genomic signals, etc.

It is of particular significance that these Micro-Organospheres survive in a biologically significant manner, allowing them to provide clinically and physiologically relevant data, particularly with respect to drug response, as will be described in FIGS. 22A-22D and 23A- 23D. In particular, the Micro-Organospheres described herein permit tissue extract/biopsy originated cells to grow exceptionally well and provide more representative data, especially as compared to organoids or spheroids. Without being bound by a particular theory, this may be because the cells may have a more constrained cell density in the Micro-Organospheres, permitting cells to communicate without inhibiting each other while sharing signals. The Micro-Organospheres also have a very large surface to volume ratio, more readily permitting transmission of growth factors and other signals to penetrate into the Micro-Organospheres (e.g., the Micro-Organospheres are less diffusion limited).

Assays

The Patient-Derived Micro-Organospheres described herein may be used in a variety of different assays, and in particular may be used to determine drug formulation effects, including toxicity, on normal and/or abnormal (e.g., cancerous) tissue. For example, drug screening may include applying Micro-Organospheres into all or some wells of multi-well (e.g., a 96-well) plate. Alternatively custom plates may be used (e.g., a 10,000 micro-well array may be formed of a 100 × 100 wells). The Micro-Organospheres (e.g., gel droplets) may be applied into, or in some variations onto the multiple microwell arrays and incubated with culture medium. The Micro-Organospheres may be cultured over the course of 3-5 days. In some variations, on day 5, the wells (e.g., micro-reactors) may then be dosed with drug compounds, e.g., based on a set of FDA-approved anticancer drugs, to examine the effects of the drug panel. For example, the drugs texted may be based on the National Cancer Institute (Division of Cancer Treatment and Diagnosis (11)) screen, consisting of 147 agents intended to enable cancer research, drug discovery and combination drug studies. On Day 7, the Micro-Organospheres may be imaged via standard fluorescent microscopy and ranked based on drug response.

An example of this assaying technique is shown in FIGS. 17A-17E.

In this example, the screening assay may be automated. This may enable repeatable and automated workflow, which may increase the number of drugs screened from a few to hundreds. FIGS. 17A-17E illustrate one example of this workflow. In FIG. 17A, a tumor biopsy is taken and a plurality (e.g., >10,000) Micro-Organospheres are formed as described above (in FIG. 17A the junction region forming the Micro-Organospheres is illustrated). Thereafter, the Micro-Organospheres may be recovered and washed (e.g., to remove the immiscible (e.g., oil) material in which they were formed. The Micro-Organospheres may then be plated into one or more microwell plates. As shown in FIG. 17C, the Micro-Organospheres may be cultured for one or more generations (e.g., one or more passages. This is shown occurring from day 0 to days 3, 4 or 5. Thereafter, the Micro-Organospheres may be screened, as shown in FIG. 17D, e.g., by applying drugs to a subset of the replicant wells. Thereafter, as shown in FIG. 17E, on day 7, the cells in the Micro-Organospheres may be imaged and/or automatically or manually scored to identify drug effects (e.g., drug screening and growth profiling).

The workflow shown in FIGS. 17A-17E may enable an integrated device to be used for growing, dosing and/or reviewing the Micro-Organospheres. In one exemplary device, freshly biopsied or resected patient tumor samples may be disassociated and seeded into gel with regents to form the Micro-Organospheres (as described above). A portion of the Micro-Organospheres formed may be cryopreserved. The rest may be recovered and incubated until seeded into microwell plates for drug testing or screening as just described. Growth and viability assays may be performed on the Micro-Organospheres, which may be imaged and tracked. Their response to drug treatments, such as IC-50, cytotoxicity, and growth curves, may be measured to identify effective therapeutics against the patient's tumor.

The methods and apparatuses described herein have numerous advantages, including reproducibility. The sample preparation process may be automated by the microfluidic sample partitioning which may reduce the need for specialized personnel for diagnostic testing and manual pipetting. This may be particularly helpful in a clinical setting. Moreover, this may enable uniformity among signal droplets, increasing assay sensitivity. In addition, these assays may minimize the time required to generate Micro-Organospheres. Based on preliminary data, these methods may be able to generate a library of over 100,000 MATRIGEL-tumor droplets (Micro-Organospheres) in less than about 15 minutes. These methods are also highly scalable, and can be multiplexed to run multiple patient biopsies in parallel.

Finally, these methods are flexable and compatible with other techniques. As a research tool, droplet-based microfluidics is generally compatible with a wide range of hydrogel materials such as agarose, alginate, PEG, and hyaluronic acid). As such, the starting gel composition can easily be modified to accompany and encourage Micro-Organospheres growth. Moreover, the droplet-size can be adjusted by modifying the size of our microfluidic device. Together, these allow a large selection of gel material composition and micro-reactor sizes.

The miniaturized assays described here, e.g., using the Micro-Organospheres, may maximizes the patient tumor biopsy, enabling more drug compounds to be screened. For example, a 600 uL tumor sample can be partitioned into ~ 143,000 individual micro-reactors that are ~ 4 nL in volume. By maximizing the tissue sample, multiple experimental replicates may be examined, increasing statistical power. These techniques may allow the inspection of intra-tumor heterogeneity, drug perturbation and identify rare cellular events, such as drug resistance. The Micro-Organospheres may generally be compatible with downstream assays including single cell RNA transcriptome analysis and epigenetic profiling. In addition, by maximizing the tissue (e.g., biopsy) sample efficiency as provided by the Micro-Organospheres, a portion of the Micro-Organospheres may be banked (e.g., by cryopreservation for biobanking) for future novel drug assays and/or for confirmation analysis, including genetic screening.

Figure 18:
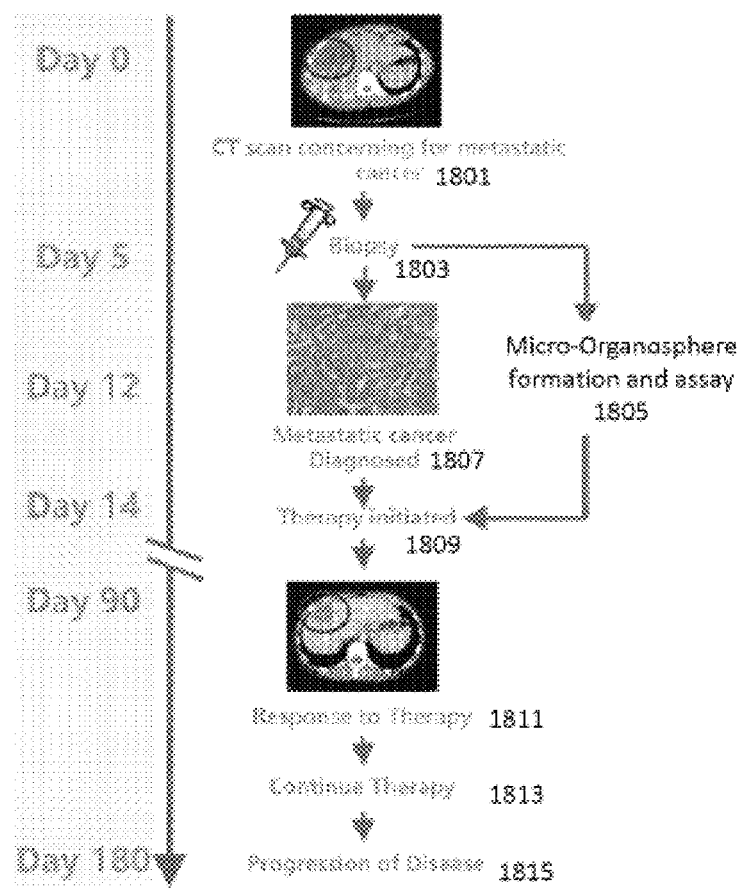
FIG. 18 schematically illustrates an example of a method for treating a patient including the formation and use of a plurality of Patient-Derived Micro-Organospheres as part of the treatment procedure.
Figure 19:
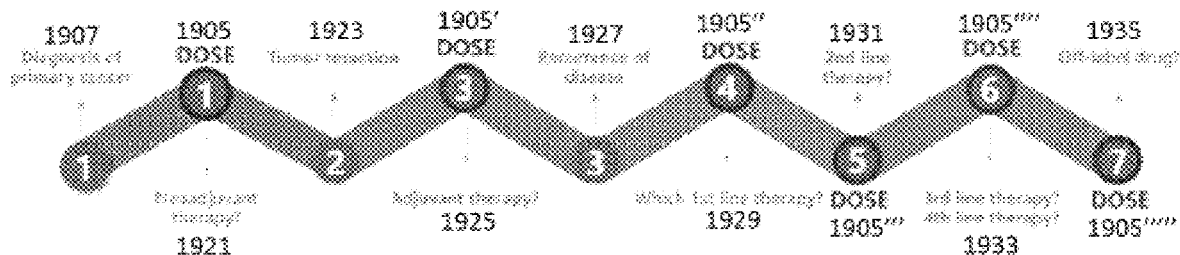
FIG. 19 schematically illustrates an example of a method for treating a patient including multiple iterations of rapidly forming and assaying a plurality of Patient-Derived Micro-Organospheres as part of the treatment procedure.

For example, FIGS. 18 and 19 illustrate example of therapeutic methods that use the methods and apparatuses, including the Micro-Organospheres, described herein. For precision and personalized medicine, these methods and apparatuses can be used as a clinical indicator for appropriate drug selection to improve clinical outcome and drug response. As one embodiment, a patient diagnosed with metastatic cancer will take a biopsy for histopathology and for screening of a plurality of Micro-Organospheres formed from a biopsy as described herein. Within 7~10 days, the screening may be performed from the biopsy to identify the most effective standard-of- care therapy so the patient can start treatment around 14 days.

An example of this is illustrated in FIG. 18. In this example, the tumor may be identified at day 0 (e.g., by CT scan) 1801, and a biopsy taken 1805 at day 5, and on the same day hundreds, thousands, or tens of thousands of Micro-Organospheres can be formed and cultured for 1-5 days and screened 1805 to identify one or more drug compositions that can be used. This same step (forming the Micro-Organospheres and screening) may be used to guide precision medicine at multiple clinical decision points throughout disease progression. In this example, therapy using the identified one or more drug compositions may be started on day 14 1809, and the patient may later be monitoring during the course of treatment (e.g., a follow-up CT scan on about day 90) to confirm that the tumor is responding to the treatment 1811. If so, the therapy may be continued 1813 and the ongoing progress monitored 1815.

As mentioned, the use of Micro-Organospheres to assay may be repeated at multiple point throughout treatment during the course of the treatment. This is illustrated in FIG. 19. For example, when a patient is first diagnosed 1907 with a resectable primary tumor, this technique (e.g., generation of Micro-Organospheres and screening 1905) can be used to determine the most effective neoadjuvant therapy 1921. Thus, a biopsy may be taken and hundreds, thousands, or tens of thousands of Micro-Organospheres may be formed and screened with a panel of potential drug compositions. Once the primary tumor is resected 1923, this technique 1905' may indicate whether and which adjuvant therapy should be chosen 1925. If recurrence or metastasis happens after the surgical removal of the primary tumor 1927, the same technique (e.g., generating and screening Micro-Organospheres from a fresh biopsy 1905", 1905''', 195'''') can be used to guide standard-of-care therapy, including 1st 1929, 2nd 1931, and 3rd line 1933 therapies. If the patient eventually becomes tolerant or resistant to all standard-of-care therapy, this technique 1905''''' can be performed to identify off-label drugs to treat resistant tumors 1935. This technique can also be used as companion diagnostics to identify patients for a specific treatment. Lastly, the technique can be used to derive and preserve patient-derived Micro-Organospheres to establish Organosphere-base living cancer bank for screening, genomic profiling, new drug discovery, drug testing and clinical trial design.

Because these techniques, and the generation of a huge number of Micro-Organospheres may be done relatively low-invasively (e.g., by resection or biopsy), to provide reasonably fast results from the screening, these methods may be easily adapted for standard of care. For example, the volume of cellular material from the tissue (e.g., biopsy) input is quite small, and may be dissociated into a volume of, e.g., between 10 μL to 5 ml.

In general, the use of the Micro-Organospheres described herein for screening may be automated or manually performed. Virtual any screening technique may be used, including imaging by one or more of: confocal microscopy, fluorescent microscopy, liquid lens, holography, sonar, bright and dark field imaging, laser, planar laser sheet, including high- throughput embodiments of image-based analysis methods (e.g., using computer vision, and/or supervised or unsupervised model, e.g., CNN). Downstream screening may include sampling the culture media and/or performing genetic or protein screening (e.g., scRNA-seq, ATAC-seq, proteomics, etc.) on cells from the Micro-Organospheres.

EXAMPLES

Figure 20:
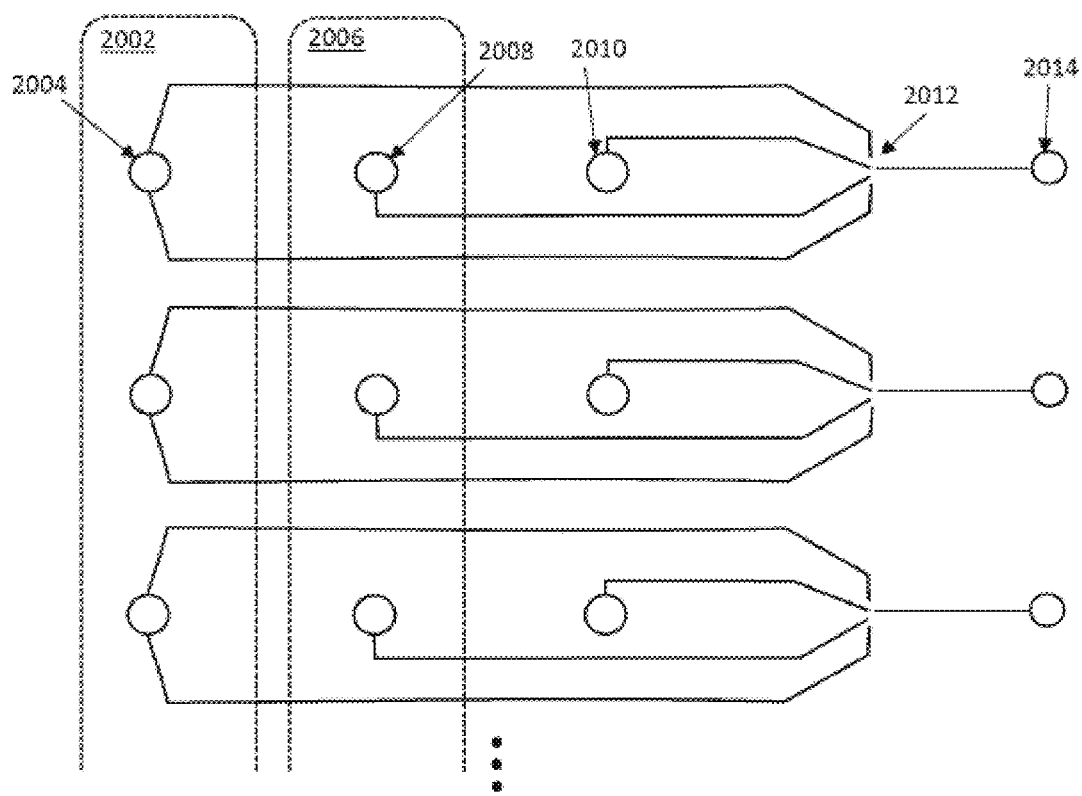
FIG. 20 schematically illustrates one variation of a portion of an apparatus for forming a plurality of Patient-Derived Micro-Organospheres as described herein.
Figure 21:
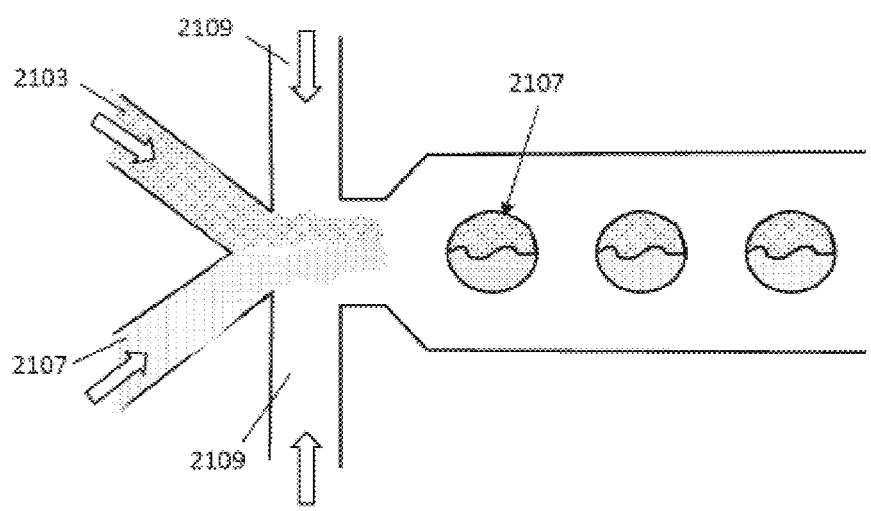
FIG. 21 schematically illustrates a method of operating an apparatus for forming a plurality of Patient-Derived Micro-Organospheres similar to that shown in FIG. 20.

FIGS. 20 and 21 illustrate another example of an apparatus for forming a plurality of Micro-Organospheres as described herein. In FIG. 20, the apparatus may include a plurality of Micro-Organosphere forming junctions, in which the immiscible material (e.g., oil) 2002 may be added to a reservoir and/or port 2004 in the device. Similarly, the unpolymerized material 2006 (in this example, including the dissociated biopsy cells and the fluid matrix material) may be added to the reservoir or port 2008 in the apparatus. In some variations a second or additional material (e.g., a biologically active agent) may be added via a third set of ports 2010. These components may be combined at a junction (similar to that described above) forming a droplet in the immiscible material that may be polymerized into the Micro-Organospheres. In FIG. 20, three (or more) parallel junctions with corresponding inputs and output are shown.

FIG. 21 illustrates the method of forming the Micro-Organospheres using an apparatus as shown in FIG. 20. In this variation the resulting Micro-Organospheres includes both the target (e.g., tumor) biopsy cells but also one or more additional biologically active agents that are combined to form the Micro-Organosphere. For example, a first channel 2103 may include the unpolymerized material (including the dissociated biopsy cells and the matrix material), a second channel 2107 includes an additional active biological material, and a pair of intersecting channels 2109, 2109' carrying the immiscible material (e.g., oil) converge at the junction to form the size-controlled droplets that are polymerized to form the Micro-Organospheres 2107.

In this example the additional active biological material may be, e.g., freezing medium (e.g., to aid in banking the Micro-Organospheres), and/or co-cultures with additional cells (e.g., immune cells, stromal cells, endothelial cells, etc.), additional supportive network molecules (e.g., ECM, collagen, enzymes, glycoproteins, biomimetic scaffolds, etc.), additional growth factors, and/or drug compounds.

Example 2: Screening Results

As mentioned above, the Patient-Derived Micro-Organospheres and methods of using them to screen for drug compositions may be used to accurately predict the response of a patient tumor to one or more drug therapies. In some cases, the use of Micro-Organospheres may provide accurate results where traditional cultured drug screening does not accurately predict drug response. For example, in FIG. 22A-22D, the Micro-Organospheres, but not a cell line, was able to correlate with patient response. In FIG. 22A, a traditional cell line dosed with drugs (e.g., Oxalipalitin) was examined; the drug line showed no effect, predicting that the tumor would be resistant to the drug at all dose ranges examined.

For comparison a plurality of Micro-Organospheres were generated from a patient biopsy, as shown in FIG. 22B. In this example, the Patient-Derived Micro-Organospheres showed significant decreases in cell survival from the tumor Micro-Organospheres, predicting drug sensitivity. In fact, when treated with the drug, the tumor responded to treatment, as shown in FIG. 22C (before treatment) and 22D (post treatment).

Example 3: Correlation Between Micro-Organospheres and Patient Response

Figure 23A:
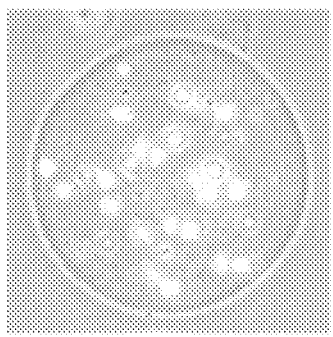
FIGS. 23A-23D illustrates another example validating the use of Patient-Derived Micro-Organospheres as described herein to identify drug resistance, showing the predicted drug response to both Oxaliplatin and Irinotecan as consistent with actual tumor response following treatment with these drugs.
Figure 23B:
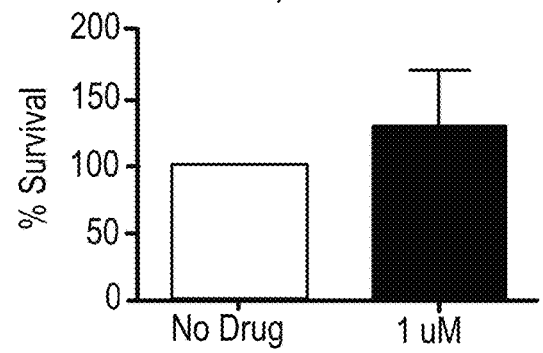
Figure 23C:
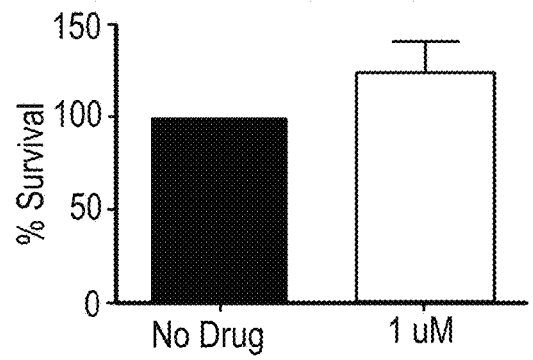
Figure 23D:
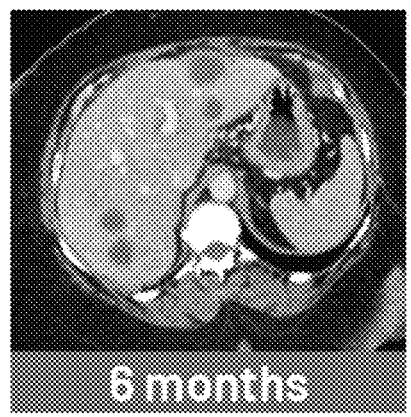

In a similar set of experiments, Micro-Organospheres were generated from biopsy material (FIG. 23A), and a drug effect screen was performed using the resulting Micro-Organospheres. FIG. 23B shows the effect of a first drug (Oxalipalatin) on these Micro-Organospheres, showing no change in the percent survival of the Micro-Organospheres in the presence of the drug, predicting drug resistance. Similarly, treatment with a second drug, Irinotecan, showed a lack of effect on the Micro-Organospheres, predicting drug resistance, as shown in FIG. 23C. The patient was treatment with both Oxalipalatin and Irinotecan, and, after 6 months of treatment, showed no response. Thus, the Micro-Organospheres correlated strongly with patient response to the standard of care drugs. In this case, the patient endured six months of side effects and toxicities that may have been avoided by the predicted response from the Micro-Organospheres, indicating (within 7-10 days from the biopsy) that the tumor would not respond to these drugs.

Example 4: Multi-Drug Screening

Figure 24:
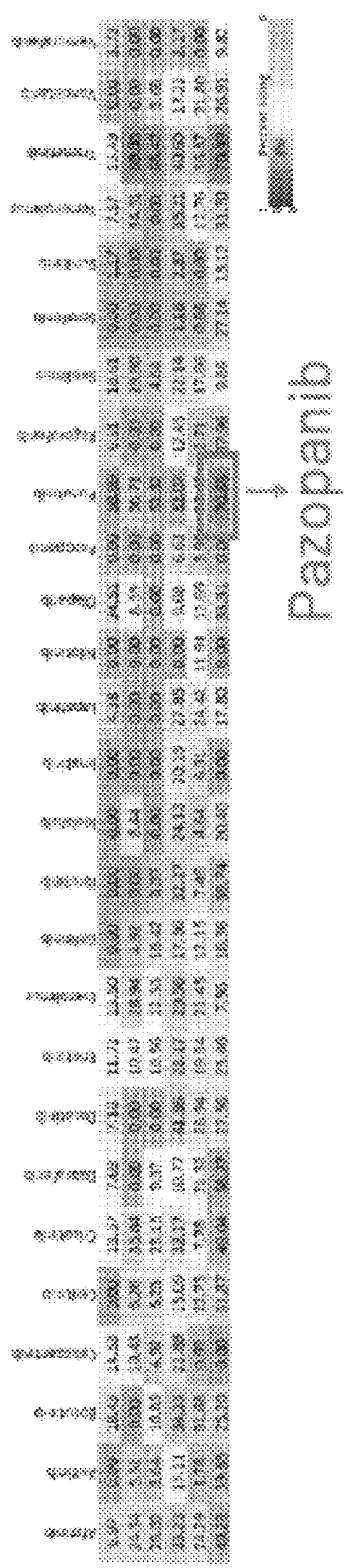
FIG. 24 illustrates one example of a drug screen using the Patient-Derived Micro-Organospheres as described herein, in which a single tumor biopsy may generate a plurality of nearly-identical Micro-Organospheres in large quantities extremely fast (e.g., within less than two weeks) and be quickly tested against a large number of drug formulations (e.g., 27 are shown) in parallel.

FIG. 24 shows an example of a panel of drug (e.g., chemotherapeutic agents) that may be generated using a Patient Derived plurality of Micro-Organospheres as described herein. In this example, a drug screen using the Patient-Derived Micro-Organospheres was run by dosing a plurality of replicates for each of a plurality of (27) drugs. A single tumor biopsy was used to generate a plurality of Micro-Organospheres in large quantities extremely fast (e.g., within less than two weeks) and these Micro-Organospheres were tested against the panel of drug formulations (e.g., 27 formulations are shown). This testing was done in parallel and could be automatically quantified (e.g., by optical detection and quantification. In this example, the drug showing the largest toxicity was Pazopanib for this particular tumor.

Combinations of drugs as wells as different drug concentrations may be examined in parallel. As hundreds, thousands, or tens of thousands of Micro-Organospheres may be generated from the same tumor biopsy, array testing of this sort is made practical by the methods and apparatuses described herein.

Example 5: Biopsy Sample Preparation

Materials: an apparatus for forming the Micro-Organospheres, as described above, including a droplet microfluidic chip (200um); Bio-rad Droplet Generation Oil for EvaGreen (catalog #186-4006), 3-5 mL per run, Perfluoro octanol (PFO), Sigma, 10% Perfluoro octanol (PFO) in Novec FIFE 7500, PBS, Cell culture media (i.e. RPMI w/ 10% FBS and 1% PenStrep), 70um or 100um filters, 50 mL conical, Petri dish.

Biopsy sample dissociation: using a biopsy sample (human/animal) to generate a dissociated sample (i.e. single cell tissue) from patient. Coat the microfluidic chip, and assemble the microfluidic chip and holder. Connect microfluidic tubing and fitting to an output (e.g., multiwall plate, 15mL Eppendorf, etc.) for the Micro-Organospheres and the waste oil.

Run the device to form the Micro-Organospheres. Remove the output (e.g., plate, Eppendorf tube, etc.) containing the droplets from the incubator (after at least 15 minutes). Remove any excess oil from the output. The droplets should be buoyant, so the oil should be at the bottom of the vial. Be careful not to remove the droplets from the tube. Add 100 uL of 10% (v/v) PFO to the output. Carefully swirl and wait ~ 1 min. Do not pipette or disturb the sample. Centrifuge at 300 g for 60 sec. Remove the supernatant (excess oil/PFO). Do not pipette or disturb the sample. Remove as much of the PFO as possible, as this chemical can reduce cell viability during culture. Add 1 mL of cell culture media. Do not pipette or disturb the sample. Centrifuge at 300g for 60 sec. Remove supernatant and any excess oil/PFO. Add 1 mL of cell culture media. Carefully pipette the sample up and down (~ 30 times) with a 1mL pipette tip. Be careful not to over pipette or disturb the droplet sample. Using a 1 mL pipette tip, place the droplet-media solution through the 70um or 100um filter (connected to a 50mL conical). Some droplets will stick to the inside of the output (e.g., a 15 mL Eppendorf). Rinse each tube with 2-3 mL of PBS and pipette up and down. Place rinsed PBS and droplets through the filter. Repeat this step twice, or until the tube looks clear, and the droplets have been transferred to the filter. Using a 1 mL pipette tip, carefully wash the filter containing the droplets with ~ 5 mL of PBS. Try and cover the entire surface area of the filter. This washing step removes any excess oil and PFO from the sample, and allows the final recovery of the gel droplets into cell culture media.

Once drained correctly (~ 1-2 minutes), carefully remove the filter from the 50 mL conical. Flip the filter upside-down and wash the back side with fresh cell culture media, and catch the solution in a fresh petri dish. This detaches the droplets from the filter, and places them in the cell culture media. It is recommended to use a 1 mL pipette tip, and wash with ~ 5 mL of media.

Check the quality of the droplets under the microscope. Most/all of the oil should be removed. If poor recovery, the sample can be re-filtered. Density of Micro-Organospheres recovered may be checked by hemocytometer.

Example 6: Renal Tissue Micro-Organosphere

In another example, Micro-Organospheres may be formed from biopsied renal tissue. For example, instruments used may include: a tube rotator or 100 µm and 70 µm cell strainer, 15 mL conical tubes, 50 mL conical tubes, Razor blades, Tweezers and surgical scissors, Petri dish (100 × 15 mm) or tissue culture dish. The reagents may include: EBM-2 media, Collagenase (5 mg/mL stock), Hank's Balanced Salt Solution (HBSS), Calcium Chloride (10 mM stock solution), Phosphate Buffer Solution (1X PBS), MATRIGEL, 0.4% Trypan Blue solution and Trypsin.

Rental tissue to be stored in a cold transport media and ON ICE at all times. 2 mL of enzymatic digestion solution may be placed in a 15 mL conical tube. Add 600 uL of calcium chloride (final concentration: 3 mM) and Add 200 uL of collagenase (final: 0.5 mg/mL). Transfer the renal sample into a petri/culture dish. Remove all excess or non-tumor tissue with sterile tissue or razor blade. Add 1 mL of the enzymatic solution to the tissue. Mince the sample into small pieces with the sterile razor blade (<2 mm2). Hold down the plate with tweezers or by hand. Transfer minced tissue and enzymatic solution back into the 15 mL tube with the enzymatic solution. Place the tube in the tube rotator or a 15 mL tube rotator between 30-60 minutes in 37° C. incubator. Remove the tube from the incubator. Quench the enzymatic digestion with at least 6 mL EBM-2 (at least 3 times the amount of enzymatic digestion solution). Pipette to mix. Place a 100 µm or 70 µm cell strainer onto a 50 mL conical tube. Transfer sample through the strainer. Transfer solution to a new 15 mL conical tube. Centrifuge the sample at 1500 rpm for 5 minutes. Discard the supernatant, leaving the cell pellet. Resuspend the pellet in 1 mL EBM-2 media. Add 10 µL cell mixture to 10 µL of Trypan Blue on a piece of parafilm and transfer to a cell counting plate or hematocytometer. Calculate cell concentration (#/mL). Centrifuge at 1500 RPM for 5 minutes and discard the supernatant, leaving the pellet. Resuspend cell pellet in 50 uL of MATRIGEL per $1.25 \times 10^5$ cells. Perform ON ICE. Plate 50 uL domes of MATRIGEL-cell suspension in the center of wells in a pre-warmed 24-well flat bottom plate. Transfer the plate to a 37° C. cell incubator and incubate for at least 20 minutes. Confirm that domes are polymerized. Gently add 500 µL of prewarmed EBM-2 media down the wall of the well. Incubate in 37° C. incubator. Perform a full media change every 2 days to expand Micro-Organospheres.

Example 7: Liver Micro-Organosphere

As mentioned, Micro-Organospheres may be formed from normal (e.g., non- cancerous) and/or abnormal tissue. For example, FIGS. 25A-25 and 26A-26B illustrate one example of Micro-Organospheres formed from a mouse liver tissue that has been dislocated, combined with a fluid matrix material to form an unpolymerized mixture, then a droplet of the unpolymerized mixture was polymerized to form the Micro-Organospheres. In this example, the Micro-Organospheres have a diameter of about 300 µm. In FIGS. 25A-25B the Micro-Organospheres were formed with a single cell per droplet. In FIGS. 26A-26B the Micro-Organospheres were formed with 25 cells per droplet. In FIG. 25A the Micro-Organospheres are shown one day after forming; FIG. 25B shows the Micro-Organospheres after ten days in culture. Cells in some of the Micro-Organospheres have divided, forming clusters exhibiting structure; other Micro-Organospheres included cells that were slower to divide or that did not divide. Similarly, in FIGS. 26A-26B the Micro-Organospheres initially including about 25 cells in each Micro-Organospheres. After ten days in culture, some of the Micro-Organospheres showed a great deal of cell growth, forming structures, while other Micro-Organospheres showed only modest growth. In both cases, the cells within the Micro-Organospheres have been found to exhibit properties characteristic of the original tissue (e.g., liver cells) from which they originated.

Figure 27A:
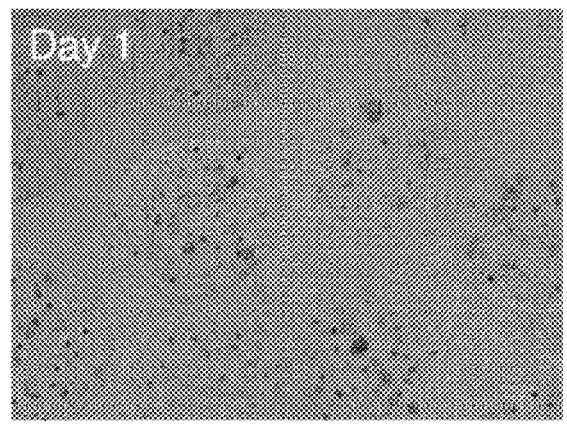
FIGS. 27A-27C illustrate examples of human liver Micro-Organospheres formed from human liver tissue.
Figure 27B:
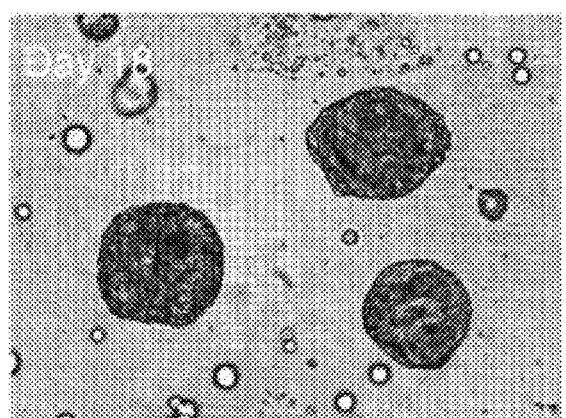
Figure 27C:
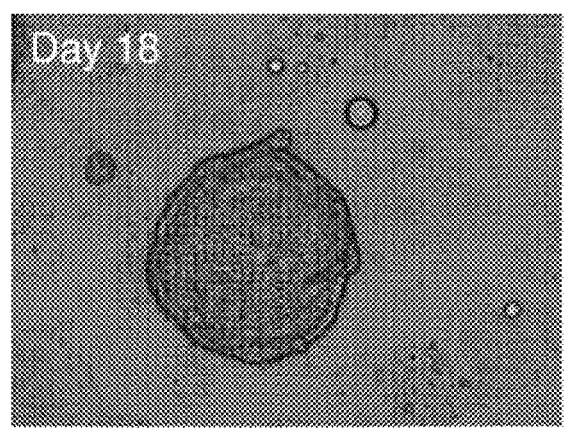

The same procedure was successfully performed on human liver tissue, as shown in FIGS. 27A-27C. In this example the Micro-Organospheres were initially formed with about fifty cells, as shown in FIG. 27A. By day 18 in culture, some of the Micro-Organospheres showed cells having clusters and forming structures, while others had smaller structures or the cells did not divide.

Example 8: Cultured Cell Micro-Organospheres

In addition to primary tissues, e.g., removed from a patient immediately or shortly before forming Micro-Organospheres, Micro-Organospheres may be formed from cultured cells or cells, including either 2D cultured cells or 3D cultured cells.

Figure 28A:
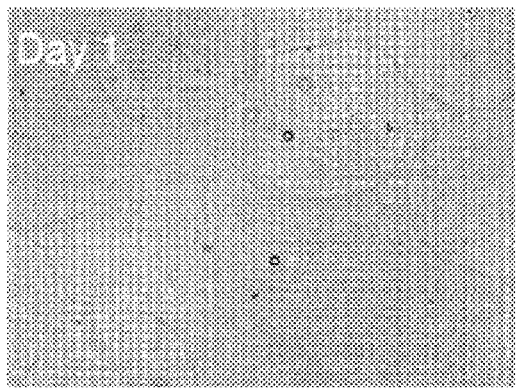
FIGS. 28A-28D show examples of Micro-Organospheres generated from a patient derived xenograft tumor line, having diameters of 300 µm, and 1 cell per Organosphere
Figure 28B:
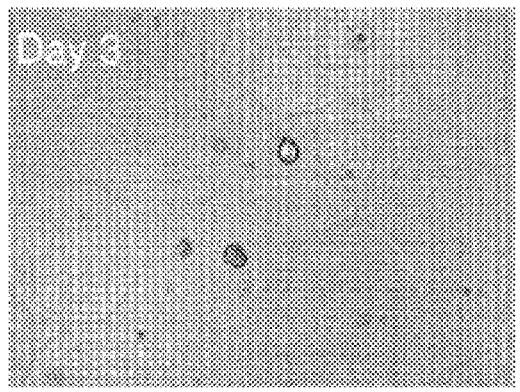
Figure 28C:
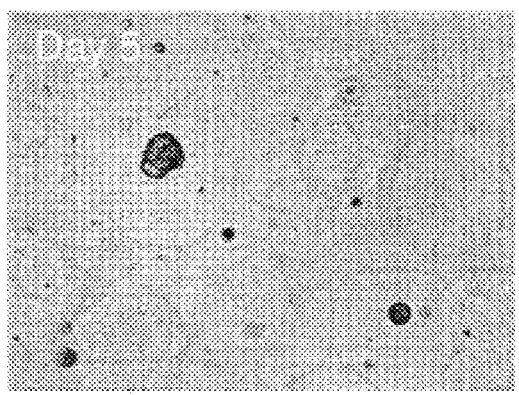
Figure 28D:
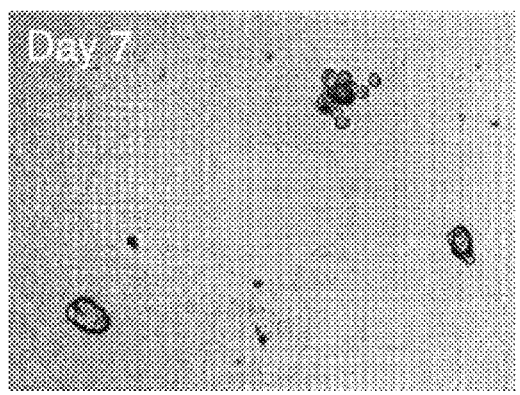

In some variations, the Micro-Organospheres may be formed from cell lines grown as part of a Patient Derived Xenograft (PDX). For example, FIGS. 28A-28D illustrate Micro-Organospheres formed from cultured PDX240 cells. PDX240 cells are a Patient Derived Xenograft (PDX) tumor cell line (numbered 240 based on patient source) that were human tumors grown in immunodeficient mice (PDX) to form in vivo tumors. The xenograft tissue was extracted dissociated, and used to form Micro-Organospheres as described above. In this example a single cell was included in each Micro-Organospheres as it was formed. FIG. 28A shows the Micro-Organospheres after one day in culture, while FIG. 28B shows the Micro-Organospheres after three days in culture and FIGS. 28C and 28D show the Micro-Organospheres after five and seven days in culture, respectively. With progressive time in culture, at least some of the Micro-Organospheres show the cells dividing and forming structures.

Figure 29A:
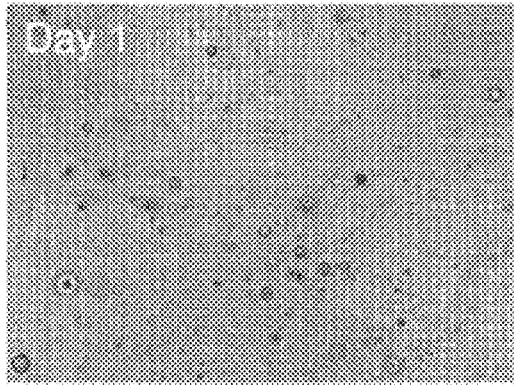
FIGS. 29A-29D show examples of Micro-Organospheres generated from a patient-derived xenograft model, having diameters of 300 µm, and 5 cell per Organosphere.
Figure 29B:
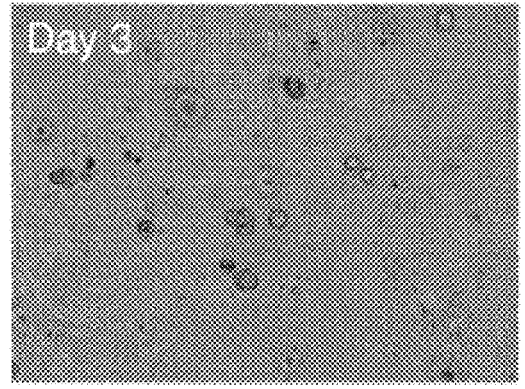
Figure 29C:
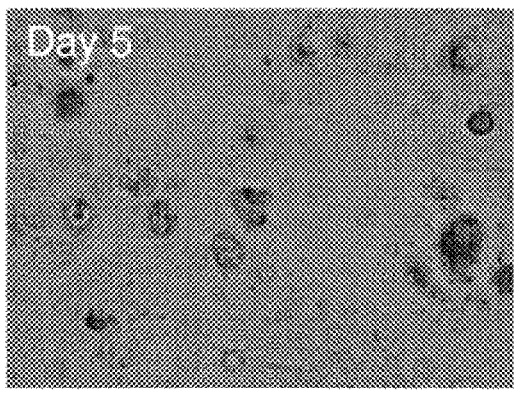
Figure 29D:
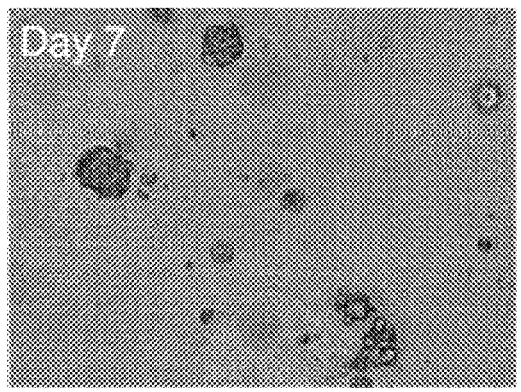

FIGS. 29A-29D show a similar experiment in which five PDX240 cells were initially included in each droplet forming each of the Micro-Organospheres. With time in culture (e.g., from day 1, day 3, day 5 and day 7, as shown in FIGS. 29A-29, respectively) the cells may divide and form structures.

Example 9: Comparison of Micro-Organospheres with Traditional Organoids

Organoids were formed from Patient Derived Xenograft cells (including the PDX240 cells described above and a second PDX cell line, PDX19187) and were compared with Micro-Organospheres formed using the same cells. The organoids were formed using conventional techniques in which a large mass of MATRIGEL in a well or dish was seeded with cells and cultured until growth was confirmed. Micro-Organospheres were generated from the traditional organoids.

Figure 30:
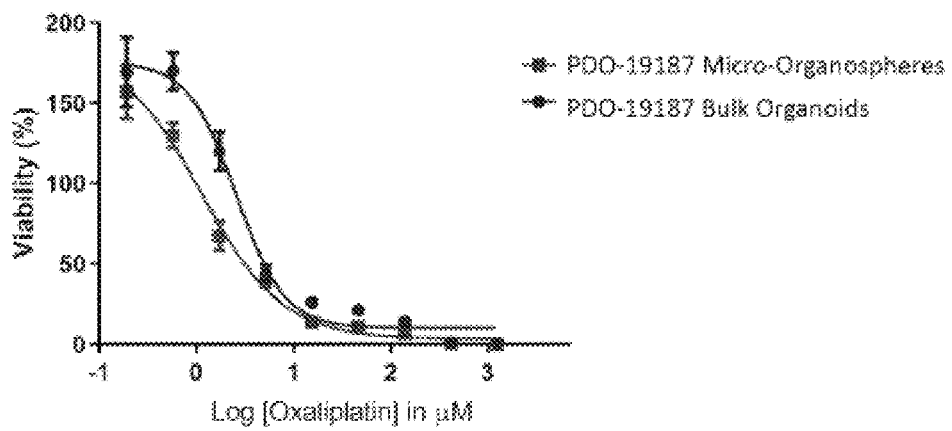
FIG. 30 is a graph comparing the responses of traditional organoids and Micro-Organospheres formed from a colorectal cancer patient-derived organoid to Oxalipalatin, showing a comparable response for the traditional organoids and Micro-Organospheres.
Figure 31:
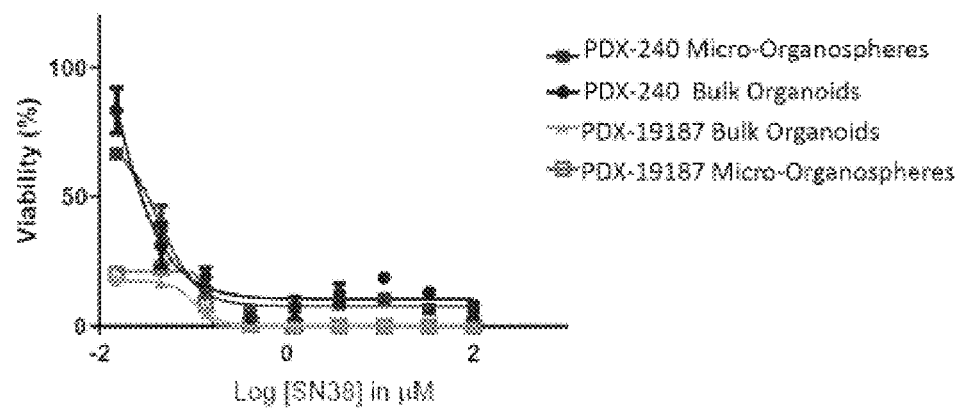
FIG. 31 is a graph comparing the responses of traditional organoids and Micro-Organospheres formed from two colorectal cancer patient-derived xenograft models to SN38 (7-Ethyl-10-hydroxy-camptothecin), showing comparable responses.
Figure 32:
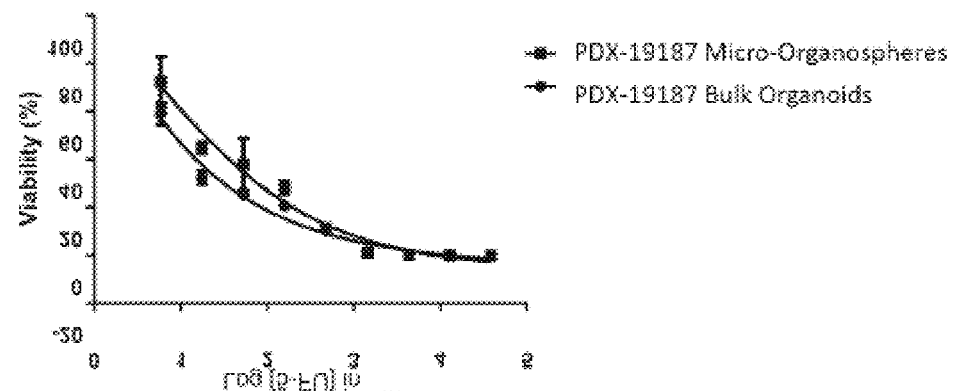
FIG. 32 is a graph comparing the responses of traditional organoids and Micro-Organospheres formed from a colorectal cancer patient-derived xenograft model to 5-FU (Fluorouracil), showing comparable responses.

Both traditional ("bulk") organoids and the Micro-Organospheres were then treated with the same drugs (e.g., Oxaliplatin or SN38) and cell viabilities were measured after 3 days of treatment. The drug response curves shown in FIGS. 30 and 31 were generated, and show similar response curves. For example, in FIG. 30, the drug response curves of PDO19187 bulk organoids and Micro-Organospheres showed similar response curves to Oxaliplatin concentration, as did PDX240 bulk organoids and Micro-Organospheres. In FIG. 31, the drug response curves for both PDX19187 and PDX240 also showed similar results for both bulk organoids and Micro-Organospheres for SN38. FIG. 32 shows response curves for another anit- cancer drug, 5-FU (Fluorouracil), again showing similar drug response curves for both PDZ- 19187 and PDX-240 traditional organoids and Micro-Organospheres.

Thus, the Micro-Organospheres described herein, which may be formed more quickly and reliably, and which may have a higher overall survival rate as compared to traditional organoids, may provide drug responses that are comparable to those of bulk organoids formed using the same cells. However, as described herein, the Micro-Organospheres may be used more quickly and may be formed in much larger numbers.

Example 10: Drug Effects on Micro-Organosphere

In general, the Micro-Organospheres described herein may be used to peroform one or more assays, including toxicity assays. Any appropriate assay may be performed, as the results determined by analysis of the tissue (e.g., cells, tissue structures) suspended within the Micro-Organosphere. The Micro-Organospheres described herein may be assayed or analysed optically, chemically, electrically, genetically, or in any other manner known in the art.

Optical (either manual or automatic) detection may be particularly useful and may include optically analyzing the effects of one or more drug formulations on the tissue (including cells, clusters of cells, structures of cells, etc.) within the Micro-Organospheres. In some variations, as mentioned above, the drug formulation may be assayed for cell death (e.g., number and/or size of tissues within the Micro-Organospheres tested. In other variations, the Micro-Organosphere may be assayed for cell growth, including reduction in the size, type and/or rate of growth. In some variations, the Micro-Organosphere may be assayed for changes in the tissue structures formed.

Figure 33A:
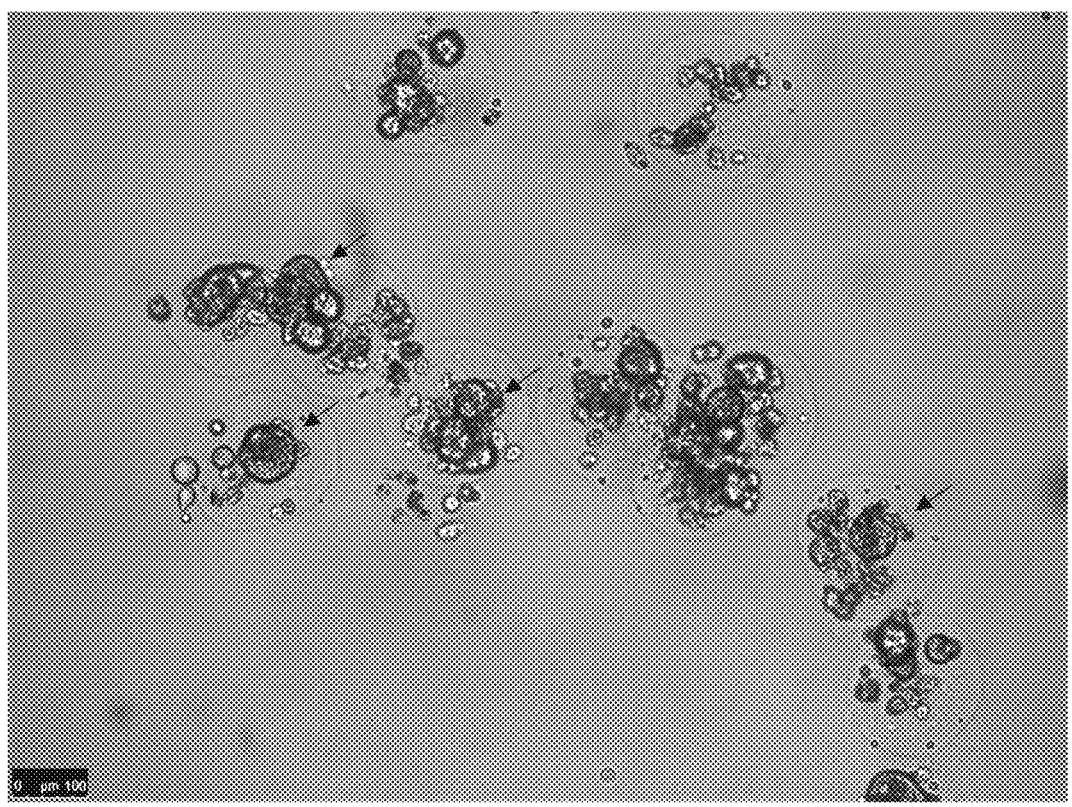
FIGS. 33A and 33B show examples of toxicity assays using mouse liver Micro-Organospheres.
Figure 33B:
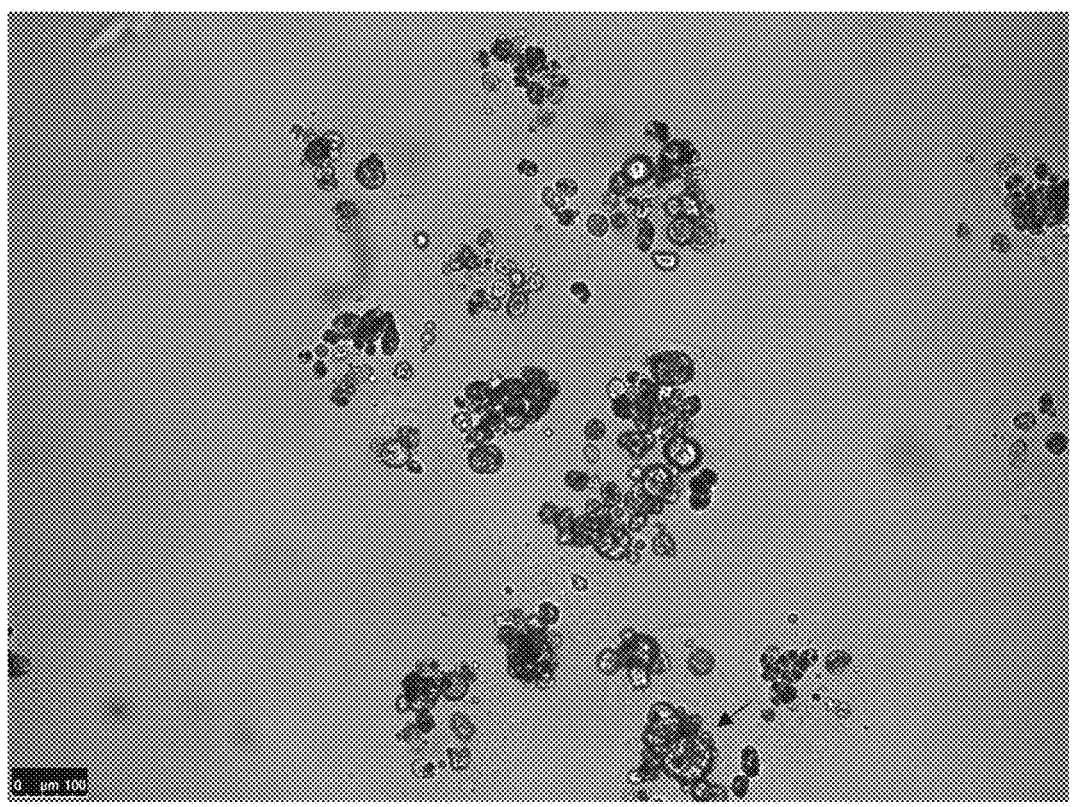

For example, FIG. 33A-33B illustrate the effect of one drug formulation, in this example, acetaminophen (10 mM) on mouse liver Micro-Organospheres. FIG. 33A is a control group, in which the Micro-Organospheres were not treated, showing tissue within the Micro-Organosphers (arrows) grown when cultured. FIG. 33B shows a similar set of Micro-Organosphere formed from mouse liver that were instead treated with 10 mM acetaminphin. In the control group the tissue structures within the Micro-Organosphere are relatively large as compared with the treatment group. The tissue in most of the Micro-Organospheres of the acetaminiphin is smaller and contains many dead cells.

Figure 34A:
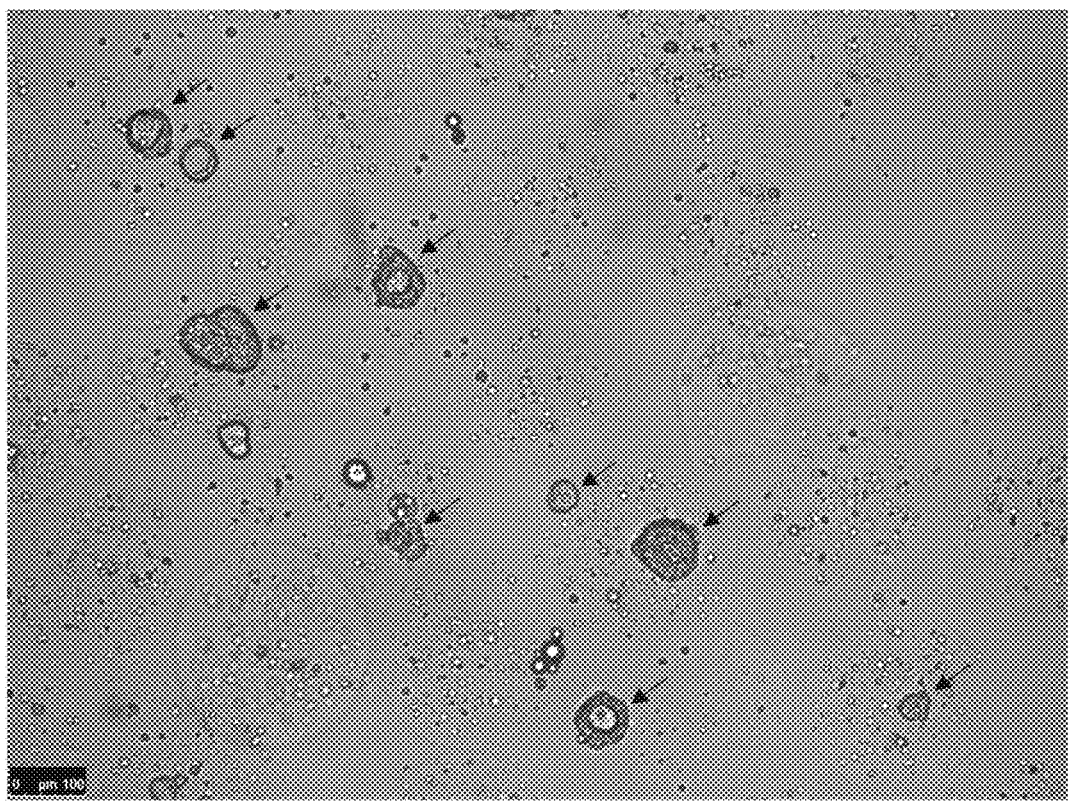
FIGS. 34A and 34B show examples of toxicity assays using human liver Micro-Organospheres.
Figure 34B:
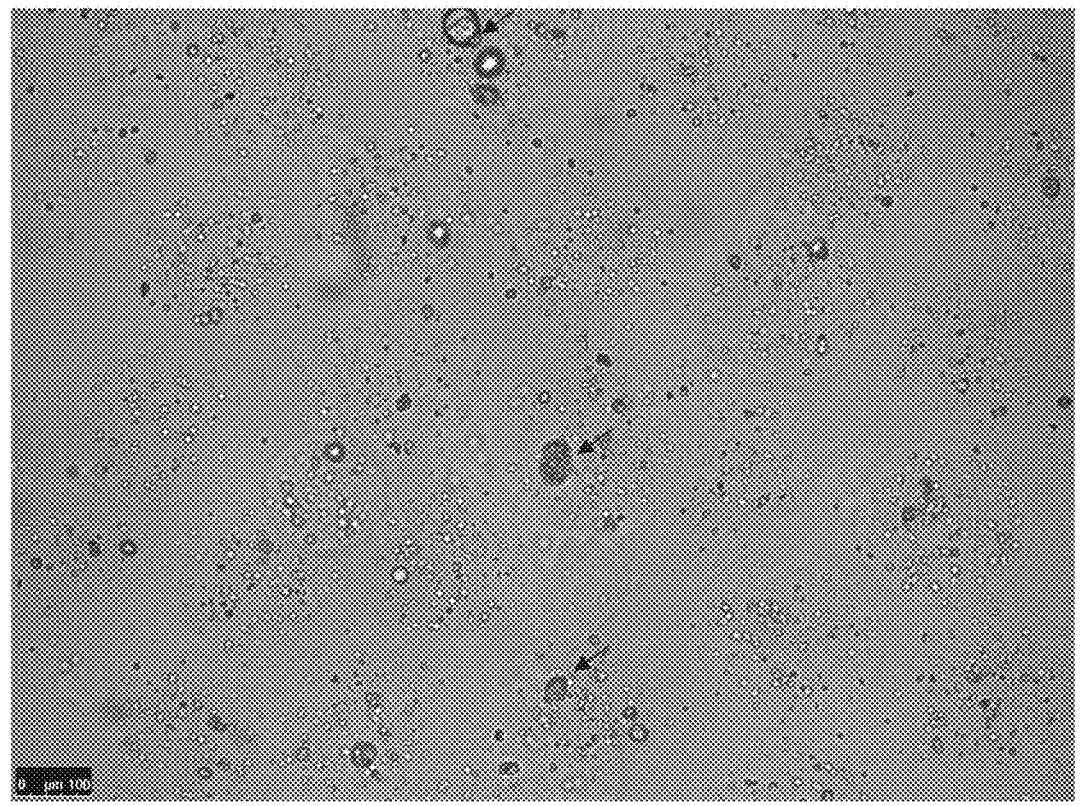

Similarly, FIGS. 34A-34B also show toxicity assays using human liver Micro-Organospheres. FIG. 34A shows typical human liver Micro-Organospheres observed in the control group including tissue structures (indicated by the arrows) formed therein. FIG. 34B shows the treatment group, in which the human liver Micro-Organospheres are treated with acetaminophen (10 mM). The tissue in the treated Micro-Organospheres showed a significant increase atypical tissue structures (arrows) and debris, as compared to the control group.

Any of these reviews, including optical reviews, may be scored, graded, ranked, or otherwise quantified. For example, in FIGS. 33A-33B and 34A-34B, the results of these two assays may be quantified to indicate the size difference, number of live/dead cells/tissue, and the like. In some variations, scoring may be automated.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/− 0.1% of the stated value (or range of values), +/− 1% of the stated value (or range of values), +/− 2% of the stated value (or range of values), +/− 5% of the stated value (or range of values), +/− 10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method, the method comprising:
combining a dissociated freshly biopsied or resected tissue sample and a fluid matrix material comprising a substrate basement membrane matrix to form an unpolymerized mixture, wherein the dissociated tissue sample comprises a single biopsy or resected patient sample;
maintaining a temperature of the unpolymerized mixture at less than 25 degrees C. and maintaining a temperature of an immiscible fluid that is immiscible with the unpolymerized mixture at greater than 25 degrees C.;
forming a plurality of spherical droplets of the unpolymerized mixture by driving a continuous stream of the unpolymerized mixture traveling at a first flow rate across one or more streams of the immiscible fluid traveling at a second flow rate that is less than the first flow rate;
polymerizing the droplets within the immiscible fluid to form a plurality of Patient-Derived Micro-Organospheres each having a diameter of between 50 and 500 p.m with between 1 and 200 dissociated cells distributed therein; and
culturing the plurality of Patient-Derived Micro-Organospheres for between 2-14 days of forming the droplets to form structured clusters of cells replicating structures of the tissue from which they were biopsied or resected.

2. The method of claim 1, further comprising modifying the cells within the dissociated tissue sample prior to forming the droplets.

3. The method of claim 1, wherein forming the plurality of droplets comprises forming a plurality of droplets of the unpolymerized mixture of uniform size with less than 25% variation in size.

4. The method of claim 1, wherein the tissue sample comprises cells that are not stem cells.

5. The method of claim 1, wherein the tissue sample comprises a biopsy sample from a metastatic tumor.

6. The method of claim 1, wherein the tissue sample comprises a clinical tumor sample, further wherein the clinical tumor sample comprises both cancer cells and stroma cells.

7. The method of claim 1, wherein the tissue sample comprise tumor cells and one or more of: mesenchymal cells, endothelial cells, and immune cells.

8. The method of claim 1, wherein combining the dissociated tissue sample and the fluid matrix material comprises disbursing the dissociated tissue sample within the fluid matrix material to a density of less than $5\times10^6$ cells/ml.

9. The method of claim 1, further comprising immediately removing the immiscible fluid from the Patient-Derived Micro-Organosphere after forming the plurality of Patient-Derived Micro-Organospheres.

10. The method of claim 1, wherein the tissue sample is combined with the fluid matrix material within six hours of removing the tissue sample from the patient.

11. The method of claim 1, wherein the temperature of the immiscible fluid is maintained at greater than 30 degrees C.

12. The method of claim 1, wherein combining the dissociated tissue sample and the fluid matrix material comprises combining the dissociated tissue sample with a MATRIGEL substrate basement membrane matrix.

13. The method of claim 1, further comprising screening the plurality of Patient-Derived Micro-Organospheres with a plurality of drug compositions within 14 days of acquiring the biopsy or resected patient sample.

14. The method of claim 1, further comprising screening the plurality of Patient-Derived Micro-Organospheres with hundreds of drug compositions within 14 days of acquiring the biopsy or resected patient sample.

15. The method of claim 1, wherein culturing comprises culturing the plurality of Patient-Derived Micro-Organospheres for between 2-14 days of forming the droplets to form budding clusters of cells replicating the structures of the tissue from which they were biopsied or resected.

16. The method of claim 1, wherein the dissociated tissue sample comprises an epithelial adenocarcinoma tissue, further wherein culturing comprises culturing the plurality of Patient-Derived Micro-Organospheres for between 2-14 days of forming the droplets to form a hollow structures of cells replicating the structures of the tissue from which they were biopsied or resected.

17. The method of claim 1, wherein the dissociated tissue sample comprises an epithelial adenocarcinoma tissue, further wherein culturing comprises culturing the plurality of Patient-Derived Micro-Organospheres for between 2-14 days of forming the droplets to form a hollow structures of cells replicating the structures of the epithelial adenocarcinoma tissue from which they were biopsied or resected.

18. A method, the method comprising:
combining, within a temperature-controlled system, a freshly biopsied or resected dissociated tissue sample and a fluid matrix material comprising a substrate basement membrane matrix to form an unpolymerized mixture, wherein the dissociated tissue sample comprises a single biopsy or resected patient sample;
maintaining a temperature of the unpolymerized mixture at less than 25 degrees C. and maintaining a temperature of an immiscible fluid that is immiscible with the unpolymerized mixture at greater than 30 degrees C.;
forming a plurality of spherical droplets of the unpolymerized mixture by driving a continuous stream of the unpolymerized mixture traveling at a first flow rate across one or more streams of the immiscible fluid traveling at a second flow rate that is less than the first flow rate;
polymerizing the droplets within the immiscible fluid by maintaining the temperature of the immiscible fluid at greater than 30 degrees C. to form more than a thousand Patient-Derived Micro-Organospheres each having a diameter of between 50 and 500 µm with between 1 and 200 dissociated cells distributed therein; and
culturing the plurality of Patient-Derived Micro-Organospheres for between 3-10 days of forming the droplets to form structured clusters of cells replicating the structures of the tissue from which they were biopsied or resected.

19. The method of claim 1, further comprising monitoring the flow rate of the unpolymerized mixture and the immiscible fluid to maintain a continuous and uninterrupted stream of unpolymerized mixture during the method.

20. The method of claim 1, further comprising pressurizing the unpolymerized material.

* * * * *

UNITED STATES PATENT AND TRADEMARK OFFICE
CERTIFICATE OF CORRECTION

PATENT NO. : 11,555,180 B2
APPLICATION NO. : 16/838010
DATED : January 17, 2023
INVENTOR(S) : Xiling Shen et al.

It is certified that error appears in the above-identified patent and that said Letters Patent is hereby corrected as shown below:

On the Title Page

Column 2, item (56), (Other Publications), Line 1, delete "Gastroinestinal" and insert
-- Gastrointestinal --.

Column 2, item (56), (Other Publications), Line 1, delete "Cutlure" and insert -- Culture --.

Column 2, item (57), (Abstract), Line 1, delete "Micro-Organosphers," and insert
-- Micro-Organospheres, --.

In the Claims

Column 41, Line 24, In Claim 1, delete "p.m" and insert -- µm --.

Signed and Sealed this
Fourteenth Day of March, 2023

*Katherine Kelly Vidal*
*Director of the United States Patent and Trademark Office*